US010512418B2

(12) United States Patent
Abe

(10) Patent No.: US 10,512,418 B2
(45) Date of Patent: Dec. 24, 2019

(54) MAGNETIC FIELD ADJUSTMENT DEVICE AND MAGNETIC RESONANCE IMAGING DEVICE

(71) Applicant: HITACHI, LTD., Tokyo (JP)

(72) Inventor: Mitsushi Abe, Tokyo (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 15/774,339

(22) PCT Filed: Jan. 26, 2017

(86) PCT No.: PCT/JP2017/002663
§ 371 (c)(1),
(2) Date: May 8, 2018

(87) PCT Pub. No.: WO2017/131070
PCT Pub. Date: Aug. 3, 2017

(65) Prior Publication Data
US 2019/0246939 A1    Aug. 15, 2019

(30) Foreign Application Priority Data

Jan. 27, 2016  (JP) .................................. 2016-012927

(51) Int. Cl.
*A61B 5/055* (2006.01)
*G01R 33/035* (2006.01)
(Continued)

(52) U.S. Cl.
CPC ............ *A61B 5/055* (2013.01); *G01R 33/035* (2013.01); *G01R 33/3875* (2013.01); *H01F 6/04* (2013.01); *H01F 6/06* (2013.01); *H01F 41/02* (2013.01)

(58) Field of Classification Search
CPC .. A61B 5/055; G01R 33/3875; G01R 33/035; G01R 33/3873; G01R 33/387; H01F 6/04; H01F 6/06; H01F 41/02
See application file for complete search history.

(56) References Cited

U.S. PATENT DOCUMENTS

2010/0244823 A1     9/2010   Abe et al.
2011/0089943 A1*    4/2011   Abe .................... G01R 33/3873
                                                              324/301
(Continued)

FOREIGN PATENT DOCUMENTS

JP          06-086763 A      3/1994
JP          08-316031 A     11/1996
(Continued)

OTHER PUBLICATIONS

International Search Report of PCT/JP2017/002663 dated Apr. 11, 2017.

*Primary Examiner* — Rishi R Patel
(74) *Attorney, Agent, or Firm* — Mattingly & Malur, PC

(57) ABSTRACT

To provide an operator with operability similar to that of conventional devices with an electromagnetic device that accurately maintains a magnetic field distribution by adjusting the magnetic field for each eigenmode obtained by singular value decomposition. The strength of a unique mode is found from a measurement magnetic field, a current for each unique mode of a negative feedback control according to the magnetic field is calculated and the current is added to each mode to obtain a current for each shim coil, and a coil current is controlled so as to reach the obtained current value. In an interface for an operator, a target for a corrected magnetic field and a magnetic field generated by a shim coil are displayed using a spherical surface harmonic function strength. Due to this configuration, a device which
(Continued)

enables accurate magnetic field adjustment while offering operability similar to conventional devices can be provided.

8 Claims, 13 Drawing Sheets

(51) Int. Cl.
*G01R 33/3875* (2006.01)
*H01F 41/02* (2006.01)
*H01F 6/04* (2006.01)
*H01F 6/06* (2006.01)

(56) References Cited

U.S. PATENT DOCUMENTS

2012/0268119 A1* 10/2012 Abe .................. G01R 33/3873
 324/307
2016/0146912 A1 5/2016 Abe

FOREIGN PATENT DOCUMENTS

| | | |
|---|---|---|
| JP | 2012-170719 A | 9/2012 |
| JP | 2013-098439 A | 5/2013 |
| JP | 2013-248081 A | 12/2013 |
| JP | 2016-036420 A | 3/2016 |
| WO | 2007/113992 A1 | 10/2007 |
| WO | 2015/005109 A1 | 1/2015 |
| WO | 2015/133352 A1 | 9/2015 |

* cited by examiner

FIG. 7
(a)
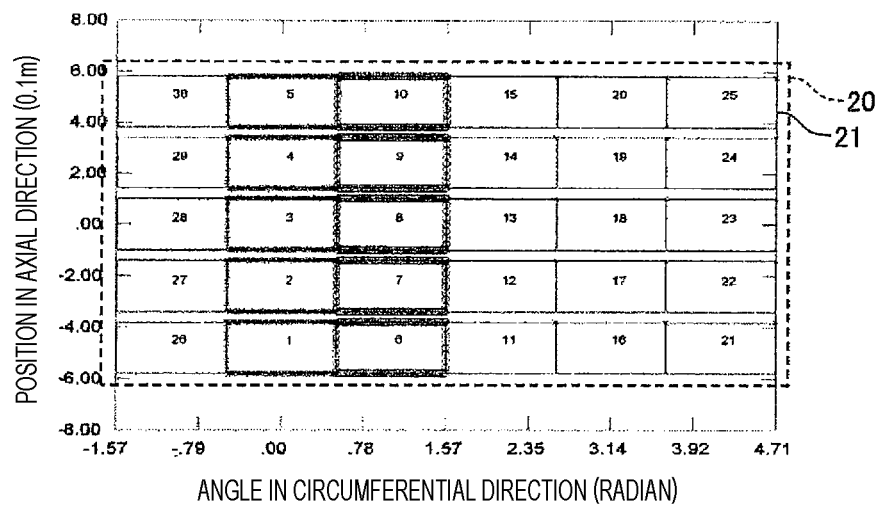
(b)
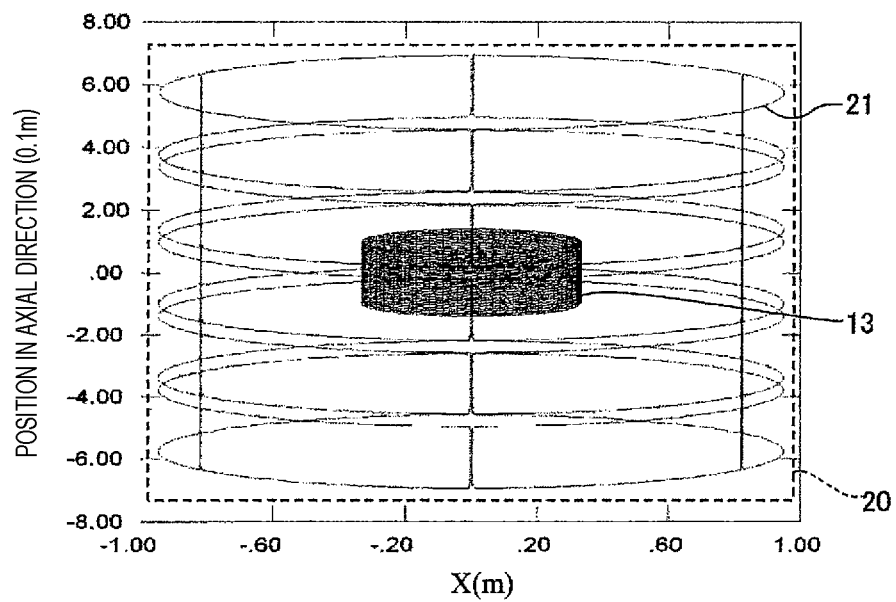

FIG. 10
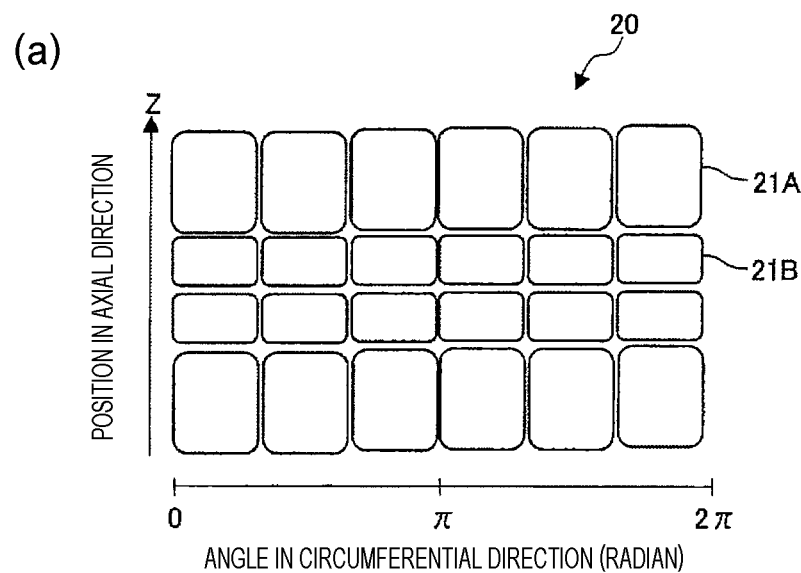
(a)
(b)
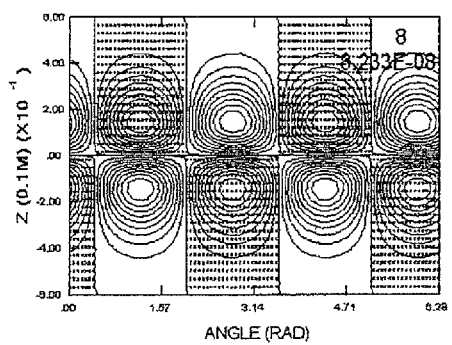
(c)
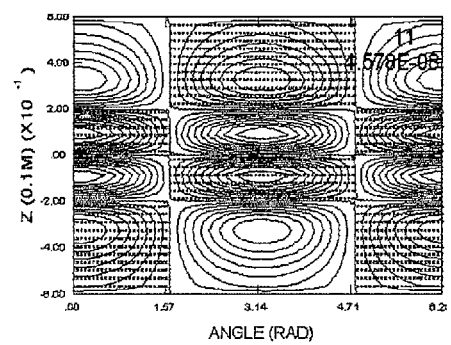

FIG. 13
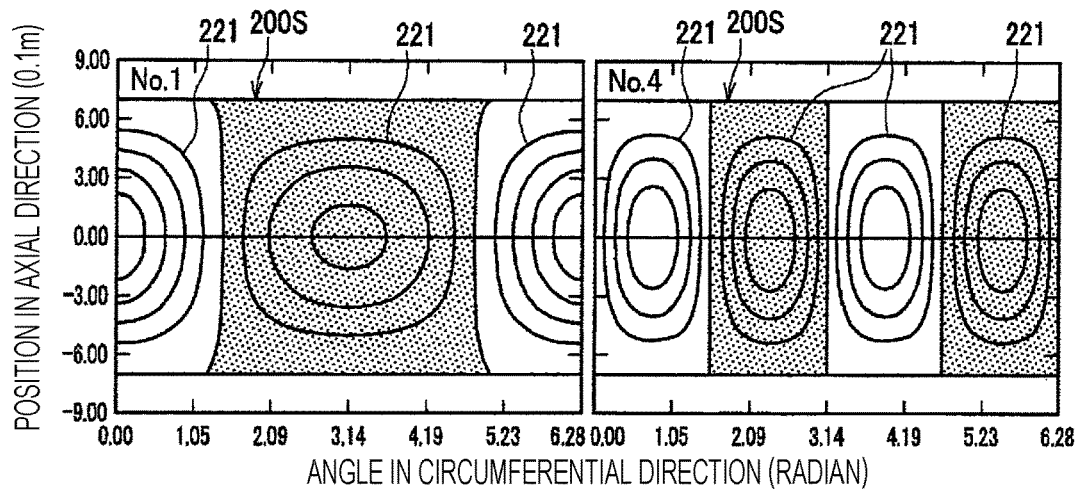
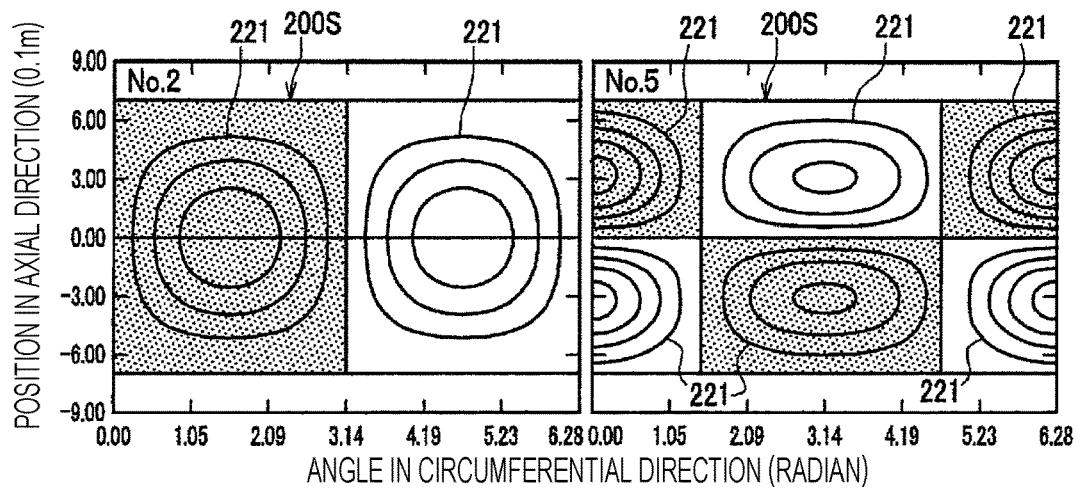
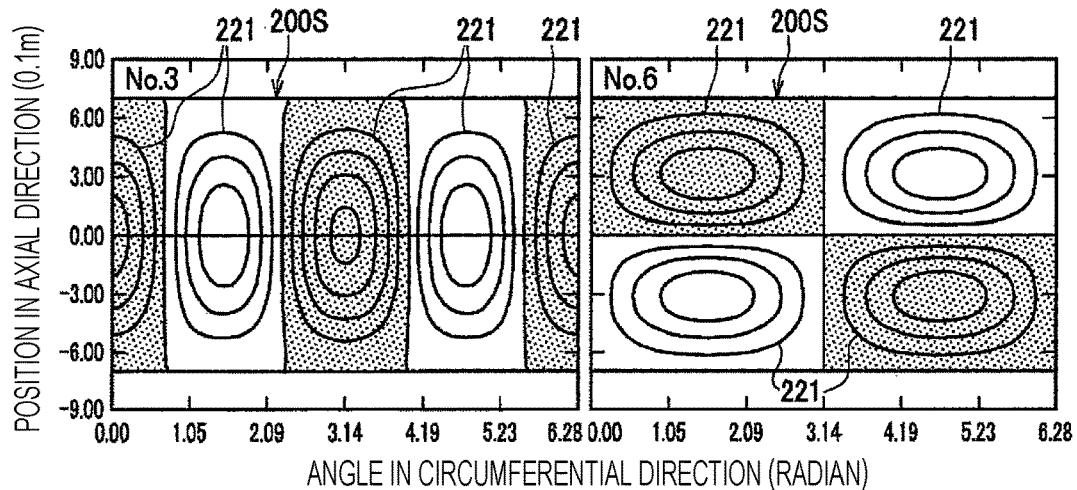
PRIOR ART

MAGNETIC FIELD ADJUSTMENT DEVICE AND MAGNETIC RESONANCE IMAGING DEVICE

TECHNICAL FIELD

The present invention relates to a magnetic field adjustment device and a magnetic resonance imaging device that adjust a magnetic field.

BACKGROUND ART

In research magnets or MRI magnets, there is demand for adjustment of a magnetic field distribution with high accuracy such that a constant magnetic field value or a target magnetic field distribution is achieved. For example, in a magnetic resonance imaging magnet (MRI, nmr), a magnetic field distribution which is constant at accuracy of 1 ppm or less and which is constant over time may be required.

When a superconductive coil is employed as a main magnetomotive force source and is supplied with a current in a permanent current mode, the magnetic flux therein is maintained and the magnetic field strength is maintained constant. A superconductive coil is used for a magnet of an MRI device or the like using such characteristics and a magnetic field is maintained substantially constant for a long time of one year or more. The MRI device also includes a fine-adjustment coil that can finely adjust a distribution of a magnetic field in a center axial direction of the magnet.

FIG. 12 illustrates a conventional fine-adjustment coil (a local coil) disclosed in PTL 1. A plurality of local coils are arranged at intervals. Accordingly, fine adjustment of a magnetic field is possible. A current distribution of each coil is calculated using a strength of a spherical surface harmonic function and a Lagrangian method of undetermined coefficients.

FIG. 13 illustrates wiring of a fine-adjustment coil disclosed in PTL 2. By allowing a current to flow in wires disposed on a cylindrical surface, a magnetic field is adjusted. It is noted that current values are determined using singular value decomposition.

CITATION LIST

Patent Literature

PTL 1: JP 8-316031 A
PTL 2: JP 2013-98439 A

SUMMARY OF INVENTION

Technical Problem

However, in PTL 1, a magnetic field which is generated by each local coil is understood as a spherical surface harmonic function including a plurality of order terms from high order terms to low order terms. In this case, interference remains, that is, a correlation is present, between a high-order function (a high order term) and a low-order function (a low order term). Accordingly, when the magnetic field is adjusted with a focus on a certain order term, an unintentional magnetic field component is also changed every time. When an amount of emitted heat is minimized, it is difficult to enhance adjustment accuracy due to a relationship of trade-off with an error magnetic field.

Particularly, in a high-magnetic-field environment, the problem becomes more severe in comparison with a case in which the magnetic field strength is low. This is because a corresponding magnitude of a current for magnetic field adjustment is required for adjusting a magnetic field distribution of a magnet with a strong magnetic field.

It is noted that FIGS. 12 and 13 illustrate an example in which local coils are arranged on a cylindrical surface, where the horizontal axis represents a position in a circumferential direction and the vertical axis represents a position in an axial direction. PTL 2 achieves more improvement in adjustment accuracy of a magnetic field than PTL 1, but since each local coil constitutes a cylindrical surface, the magnetic-field adjustment coil has a stacked structure of multiple cylindrical surfaces and thus requires a thickness in a radial direction. Accordingly, a magnetic-field adjustment coil with a decreased size is required for decreasing the size of the magnet device.

In an MRI device, a method of expanding a target magnetic field distribution with a spherical surface harmonic function, generating a magnetic field corresponding to the expansion result, and adjusting a magnetic field distribution is known. The magnetic field corresponding to the expansion result of the spherical surface harmonic function is generated by a magnetic-field adjustment coil including a plurality of coils. However, in the magnetic-field adjustment coil, in general, each coil cannot help being affected by a magnetic field resulting from another coil or an influence of induction. When correction corresponding to one expansion result is performed, a magnetic field distribution corresponding to another expansion result is affected by previously executed correction, thereby making it difficult to accurately correct a magnetic field. When interference occurs, it can be said that a current has an unnecessarily large current value.

In consideration of the above-mentioned problems, an object of the invention is to provide a magnetic field adjustment device and a magnetic resonance imaging device that can adjust a magnetic field with high accuracy even when a current is smaller than that in the related art.

Solution to Problem

The present application includes a plurality of solutions to the above problems. As one of the solutions, there is provided "a magnetic field adjustment device, at least including: a shim coil array that includes a plurality of shim coils for adjusting a static magnetic field in a magnetic field use area; a first calculation unit that determines current command values of the shim coils on the basis of eigenmodes which are obtained by singular value decomposition of a response matrix of currents flowing in the shim coils to a magnetic field; a power supply that controls the currents in the shim coils on the basis of the determined current command values; a second calculation unit that calculates correspondence between order terms which are obtained by expanding the static magnetic field in the magnetic field use area using a spherical surface harmonic function and strengths of the eigenmodes; and a display device that is connected to the second calculation unit and displays change of the static magnetic field in the magnetic field use area due to the shim coils supplied with the currents on the basis of the current command values as information on the order terms of the spherical surface harmonic function."

Advantageous Effects of Invention

According to the invention, it is possible to provide a magnetic field adjustment device and a magnetic resonance imaging device with high efficiency that can enable a user to adjust and understand a magnetic field distribution, similarly to the related art, even when shim coils using singular value decomposition is used.

BRIEF DESCRIPTION OF DRAWINGS

FIG. 7 is a diagram illustrating arrangement of a shim coil array according to an example, where FIG. 7(a) is a developed view and FIG. 7(b) is a bird's-eye view.

FIG. 10(a) is a developed view of a shim coil array according to a first modified example and FIGS. 10(b) and 10(c) are diagrams illustrating examples of a magnetic field distribution of eigenmodes of the shim coil array according to the first modified example.

FIG. 13 is a developed view of an example in which shim coils are arranged in a second conventional example.

DESCRIPTION OF EMBODIMENTS

Figure 1:
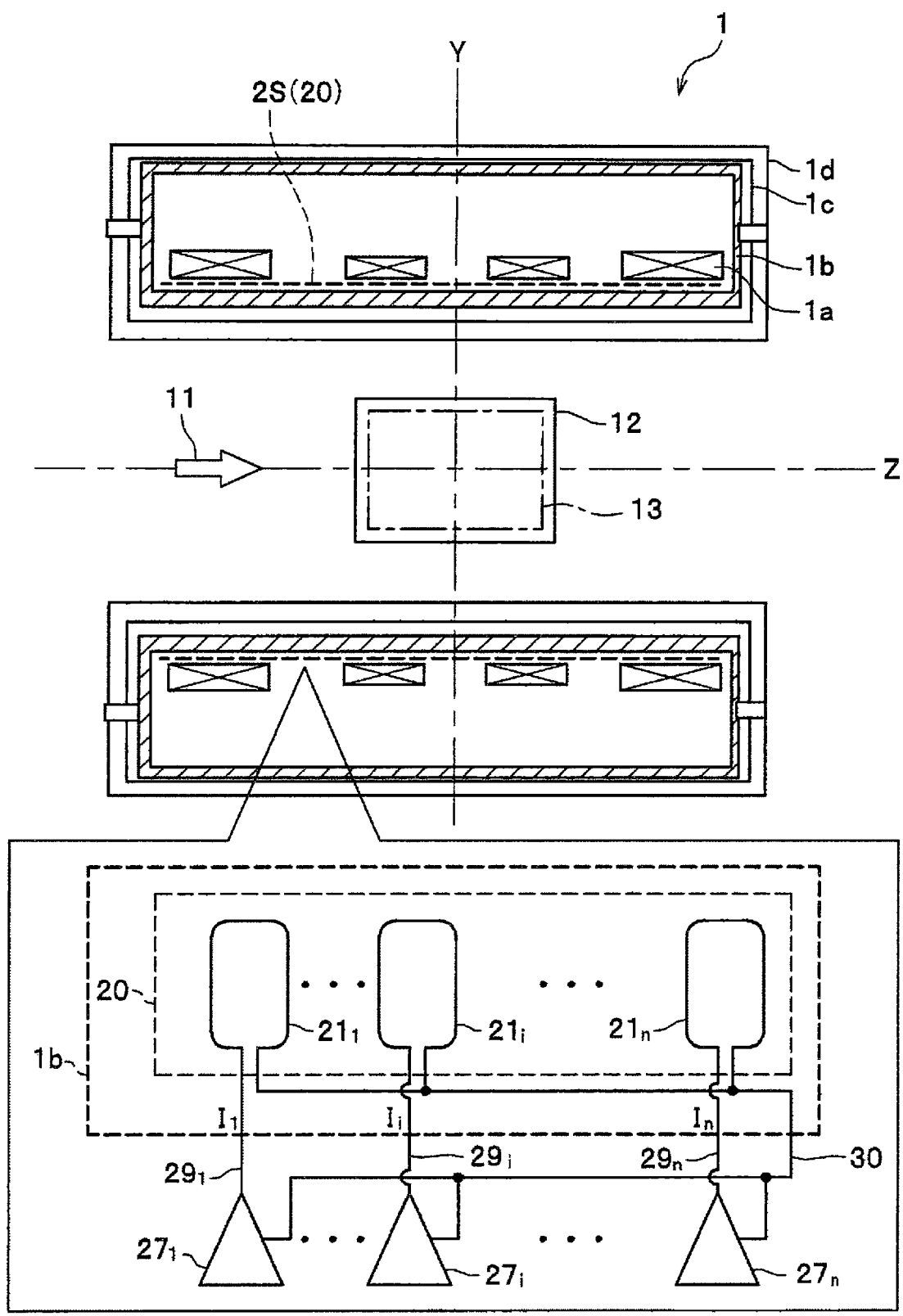
FIG. 1 is a schematic sectional view of a magnet device according to an embodiment and a diagram illustrating a shim coil connecting method.

As described in PTL 1, setting of the number of layers of shim coils (local coils constituting a magnetic-field adjustment control) to a small value (one in the example described in PTL 1) is important for simplification of a structure of a magnetic field adjustment device. However, in the method described in PTL 1, magnetic field control calculation is likely to be complicated.

On the other hand, in the method of using singular value decomposition (SVD) which is disclosed in PTL 2, magnetic field components are easy to understand. According to the singular value decomposition method, the magnetic field components constituting a correction magnetic field are calculated as eigenmodes in which a current and a magnetic field are correlated. Since the eigenmodes do not interfere with each other (have orthogonality), it is possible to simply adjust magnetic field control.

Therefore, the magnetic field adjustment device according to the embodiment employs a method of using a plurality of shim coils and applying singular value decomposition to current control of the shim coils. Accordingly, it is possible to construct a magnetic field adjustment device with high accuracy that is easy to handle.

For this method, a calculation technique disclosed in a non-patent literature (M. Abe, K. Takeuchi, "Low loop voltage startup and equilibrium control using multivariable poloidal field coils in the Hitachi tokamak HT-2", Fusion Technology, 29(1996) p. 277) by the present inventors can be referred to. In this non-patent literature, since equilibrium magnetic field control of annular plasma is performed, only a magnetic field with a uniform circumferential direction is considered. However, a magnetic field with a non-uniform circumferential direction will be considered in this time.

A disturbing magnetic field is not limited only one type, but there is a likelihood that it will include magnetic fields including various components. Accordingly, it is desirable that fine-adjustment shim coils be a set of some shim coils but not be a single coil (or a group of coils which are connected in series/parallel). There is a likelihood that a disturbing magnetic field will also be distributed in the circumferential direction.

Furthermore, it is desirable that the shim coils be independent of each other. That is, when a current flows in a certain group of shim coils and thus a current is induced in other shim coils, it is difficult to perform fine adjustment with high accuracy. When a plurality of shim coils are combined to correct a magnetic field, it is desirable that a disturbing magnetic field component can be corrected in a wide range if necessary.

That is, a shim coil group that is configured to remove components of the disturbing magnetic field in a wide range by causing a plurality of shim coils to operate independently or in combination is necessary.

The technique disclosed in the non-patent literature can be extended and used as a design technique of obtaining such a shim coil group. In the technique disclosed in the non-patent literature, a current distribution in a poloidal magnetic field coil is optimized to a current distribution for correcting a target magnetic field. In this course of calculation, a response matrix of a target area (a plasma surface in the non-patent literature) is subjected to singular value decomposition using a coil current, eigenmodes in which the current distribution and the magnetic field component form a pair are obtained, and magnetic field adjustment is performed in combination of the eigenmodes. However, the result of adjustment is understood as conventional parameters of plasma position and shape.

Figure 3:
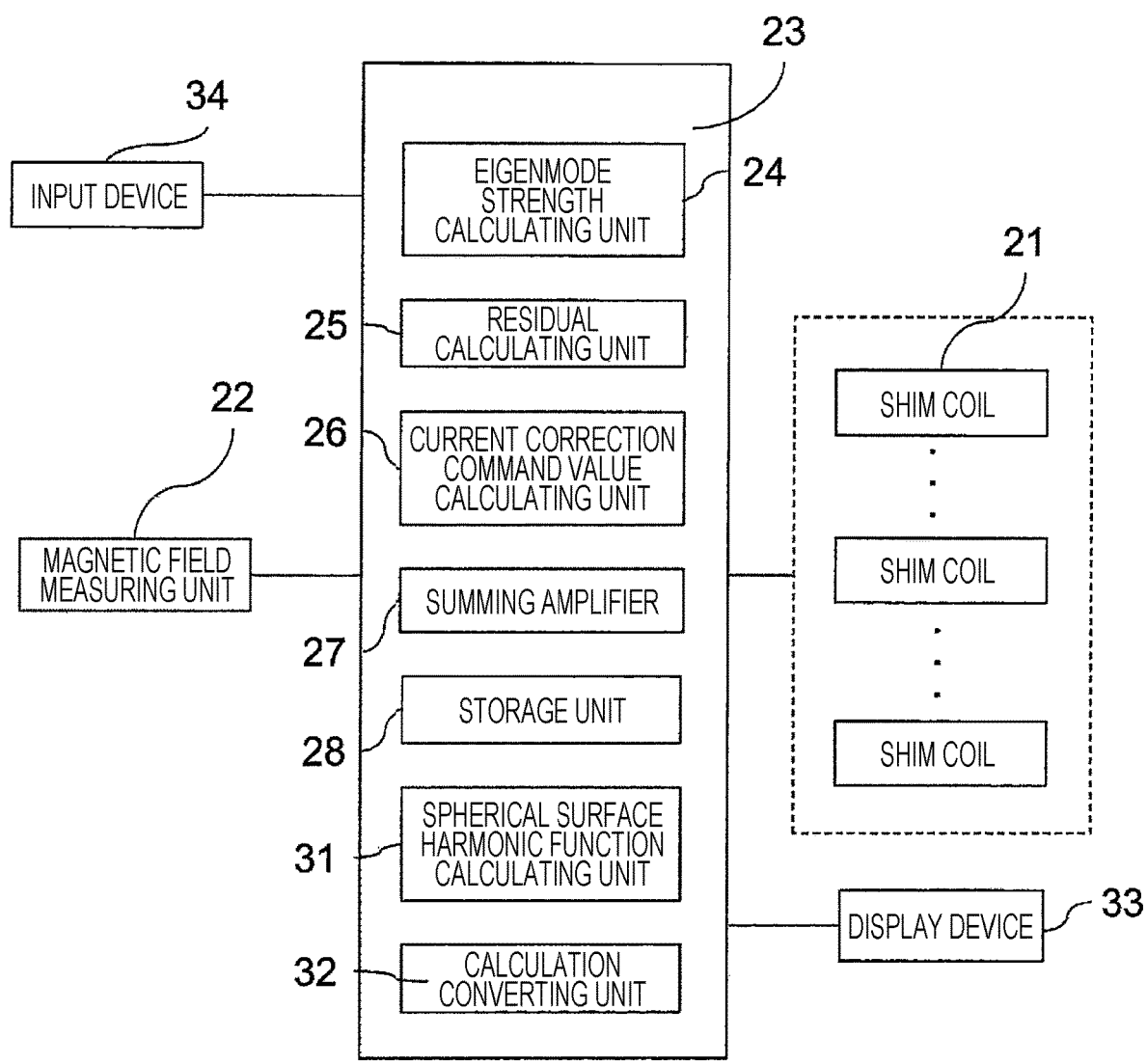
FIG. 3 is a schematic diagram illustrating a configuration of the magnetic field adjustment device according to the embodiment.

Therefore, this method is applied to a magnetic field device with high accuracy for research or a magnet device requiring a magnetic field with high accuracy such as an MRI device. The shim coils which will be described later are controlled in eigenmodes of the singular value decomposition. However, a magnetic field adjustment device with which an operator can understand a degree of correction with a strength of a spherical surface harmonic function is proposed in consideration of a case in which the operator understands a correction magnetic field using a conventional spherical surface harmonic function. The following two types of shim coils using singular value decomposition are considered. One is a shim coil as illustrated in FIG. 3 in the conventional method. In this shim coil, shim coils are manufactured to correspond to eigenmodes in a one-to-one correspondence manner. A current control circuit for a coil causes currents required for the individual eigenmodes to flow in proportion to the eigenmode strengths. The other is an array type shim coil.

The array type shim coil has a configuration in which unit shim coils which are divided in the circumferential direction are arranged densely. A magnetic field adjustment device is proposed in which each coil is a closed-current closed circuit (provided that, a power supply wiring portion is connected to a current supply circuit), each coil is connected to a current control power supply, a current value thereof is a current value overlapping in modes of current distribution of mode components of the eigenmodes, in addition, a magnetic field is measured at multiple points, each eigenmode strength is calculated from the measured values by summation in consideration of weightings of the eigenmodes of the measured values, a residual from a target eigenmode is converted into a current value, and a magnetic field is adjusted by controlling the current values.

The invention proposes that a user of the device can understand a situation of magnetic field adjustment using a spherical surface harmonic function strength as in the conventional method in addition to such shim coils using singular value decomposition.

<<Magnet Device 1 and Magnetic Field Adjustment Device 2>>

Hereinafter, an embodiment of the invention (hereinafter referred to as an "embodiment") will be described in detail with reference to the drawings appropriately. It is noted that the same elements in the drawings will be referenced by the same reference signs and description thereof will not be repeated.

A magnetic field adjustment device 2 according to the embodiment and a magnet device 1 including the magnetic field adjustment device 2 will be described below with reference to FIGS. 1 to 6. FIG. 1 is a schematic sectional view of the magnet device 1 according to the embodiment, where shim coil connection (in a speech balloon illustrated in a lower part of FIG. 1) according to the embodiment is also illustrated. The schematic sectional view illustrated in an upper part of FIG. 1 is a sectional view of the magnet device 1 taken along a plane which is formed by a Z axis which is a horizontal axis and a center axis of a superconductor coil 1a which will be described later and a Y axis which is a vertical axis.

The magnet device 1 according to this embodiment includes a plurality of (four in the example illustrated in FIG. 1) superconductor coils 1a having annular shapes with center axes (Z axis) in parallel with each other, a refrigerant container 1b, a radiation shield 1c, and a vacuum container 1d.

The superconductor coils 1a are contained in the refrigerant container 1b. The refrigerant container 1b is filled with a refrigerant for cooling the superconductor coils 1a. The refrigerant container 1b is accommodated in the vacuum container 1d. The vacuum container 1d is in a high-vacuum state to perform vacuum heat insulation between the refrigerant container 1b and the vacuum container 1d. The radiation shield 1c is provided between the refrigerant container 1b and the vacuum container 1d to curb heat transmission by radiation.

The superconductor coils 1a are coils formed of a superconductor wire and are cooled to a superconductive critical temperature or lower by the refrigerant filled in the refrigerant container 1b. The superconductor coils 1a are supplied with currents in a permanent current mode and thus function as a superconductor magnet that generates a magnetic field (a main magnetic field) in a magnetic field direction 11 indicated by an arrow in the Z-axis direction in FIG. 1. Accordingly, the superconductor coils 1a generate static magnetic field in a magnetic field use area 12 which is disposed at the center of the cylindrical magnet device 1. It is noted that in the example illustrated in FIG. 1, description will be made on the assumption that the magnet device 1 is a magnet device 1 that generates a static magnetic field in an MRI device and the magnetic field use area 12 having a cylindrical shape is set.

The magnet device 1 further includes a magnetic field adjustment device 2 (see FIG. 3 which will be described later). The magnetic field adjustment device 2 is a device that adjusts a magnetic field to improve accuracy (uniformity) of a static magnetic field in the magnetic field use area 12. Specifically, the magnetic field adjustment device 2 adjusts a magnetic field to improve accuracy (uniformity) of a static magnetic field in a set magnetic field evaluation surface 13. FIG. 1 illustrates an example in which a boundary surface of the magnetic field use area 12 is set as the magnetic field evaluation surface 13.

The magnetic field adjustment device 2 (see FIG. 3 which will be described later) includes a shim coil array 20 consisting of a plurality of shim coils 21 (see FIG. 2 which will be described later). The shim coil array 20 (the shim coils 21) is disposed on a cylindrical surface 2S (see FIG. 1) which is disposed inside in the radial direction of the superconductor coils 1a in the refrigerant container 1b. The center axis of the cylindrical surface 2S matches the Z axis (that is, the center axis of the superconductor coils 1a). The shim coils 21 are disposed in the refrigerant container 1b filled with a refrigerant and thus is preferably formed of a superconductor wire to curb emitted heat by supply of a current. Heat entering an extremely low-temperature portion (the inside of the refrigerant container 1b) from the power supply lines ($29_1$ to $29_n$, 30) of the shim coils 21 cannot be ignored. Accordingly, in this embodiment, one of the power supply lines is configured as a common power supply line 30. Accordingly, since the number of power supply lines entering the extremely low-temperature portion (the inside of the refrigerant container 1b) can be decreased, it is possible to decrease an amount of entering heat, to stably operate the superconductive magnet, and to decrease a load of a refrigerator. It is noted that this configuration will be described in detail with reference to FIG. 6 again.

The shim coil array 20 and the shim coils 21 in the magnetic field adjustment device 2 according to this embodiment will be additionally described below with reference to FIG. 2. FIG. 2 is a developed view of the shim coil array 20 of the magnetic field adjustment device 2 according to this embodiment. In FIG. 2, the horizontal axis represents an angle (radians) in the circumferential direction and the vertical axis represents a position in the axial direction of the Z axis (see FIG. 1). Moreover, the shim coils 21 are formed by winding a superconductor wire, but only a coil portion (a winding portion) of each shim coil 21 is illustrated in FIG. 2 and wires (lead wires) connected to the coil portions of the shim coils 21 and the like are not illustrated.

Figure 2:
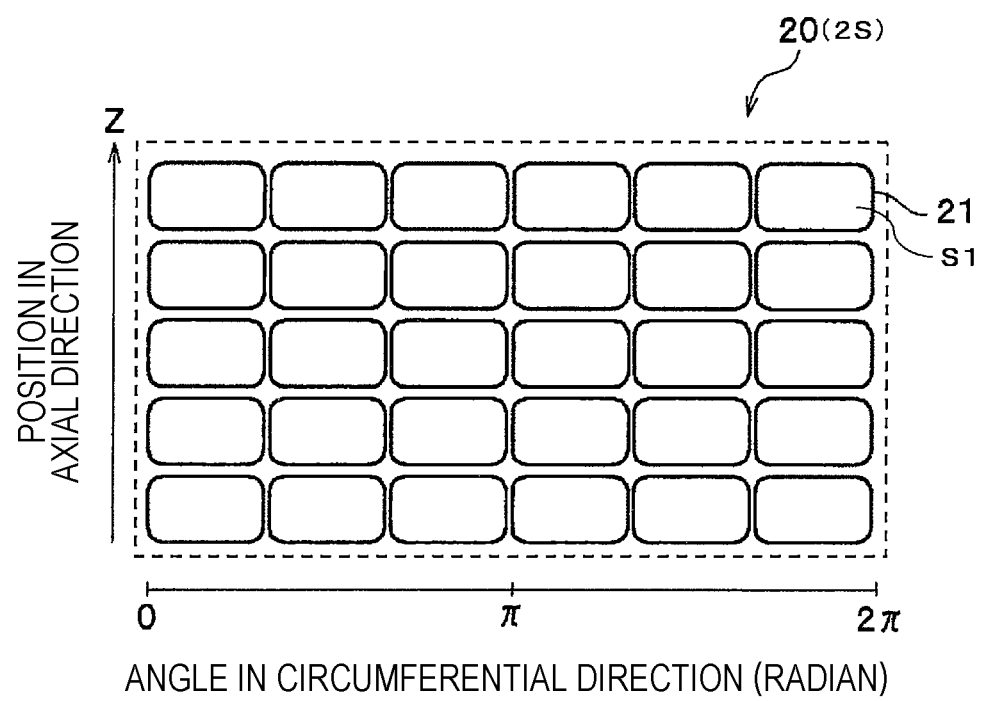
FIG. 2 is a developed view of a shim coil array which is included in a magnetic field adjustment device according to the embodiment.

In the shim coil array 20, as illustrated in FIG. 2, a plurality of shim coils 21 are arranged in the circumferential direction and the axial direction and are disposed on the cylindrical surface 2S illustrated in FIG. 1. In other words, the cylindrical surface 2S is partitioned into a plurality of areas in the circumferential direction and the axial direction, and the shim coils 21 are disposed in the divided areas to form the shim coil array 20. It is noted that in FIG. 2, an example in which total 30 shim coils 21 including six shim coils in the circumferential direction and five shim coils in the axial direction are arranged in the shim coil array 20 is illustrated.

Figure 12:
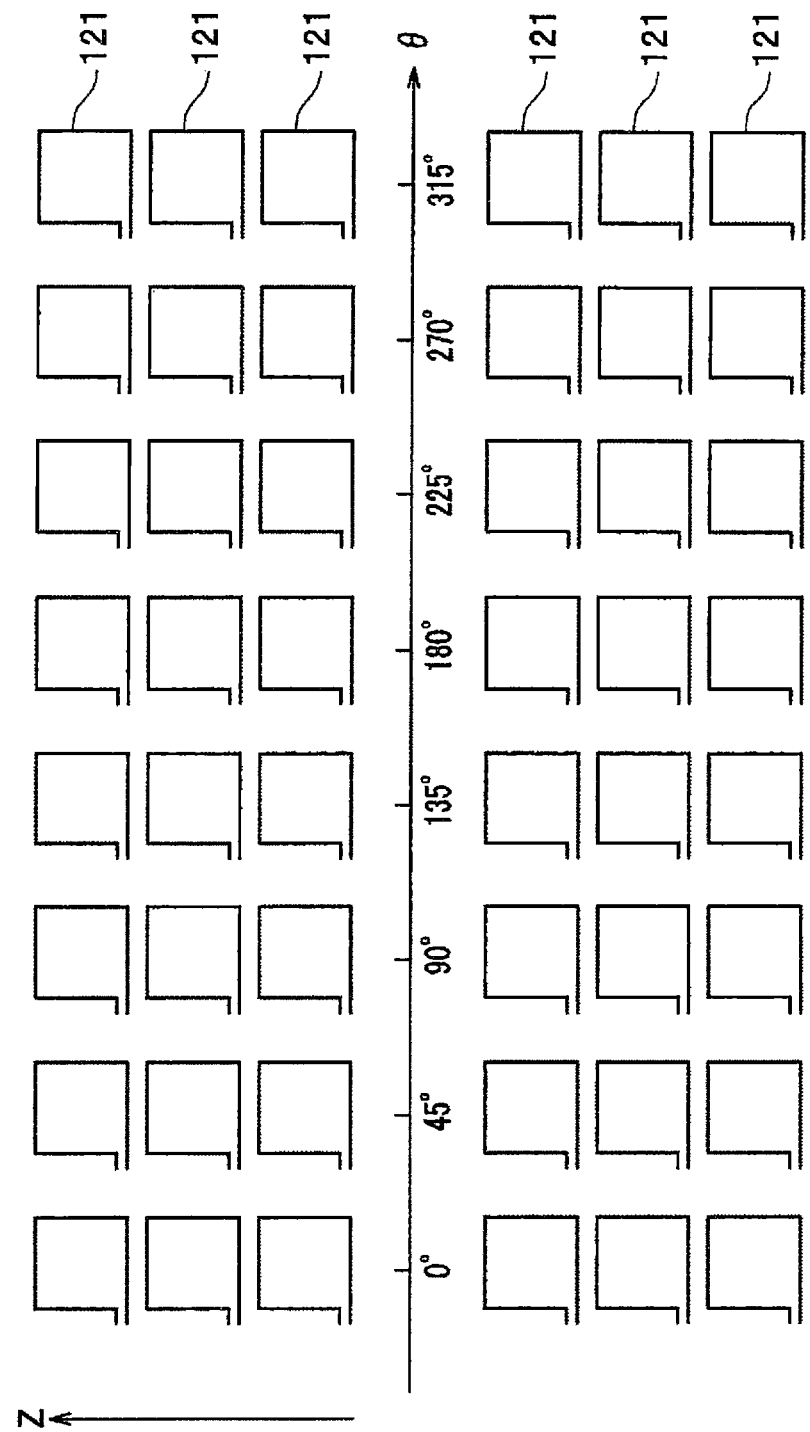
FIG. 12 is a developed view of an example in which shim coils are arranged in a first conventional example.

In a first conventional example, as illustrated in FIG. 12, wide gaps are between shim coils 121 and neighboring shim coils 121. On the other hand, in the shim coil array 20 according to this embodiment, the shim coils 21 are arranged densely as illustrated in FIG. 2.

Here, since a magnetic moment increases in proportion to the area of each coil, it is preferable that the shim coils 21 be arranged without a gap. Actually, however, due to limitation by a support structure of the shim coils 21, the size of a sectional surface of a coil conductor, or the like, an occupation ratio cannot be set to 100%. Here, when a ratio of the sum of areas surrounded by each shim coil 21 (a coil center line) (for example, an area S1 surrounded by each shim coil 21×30) and an area of a coil arrangement surface (an area of the cylindrical surface 2S) is equal to or greater than 80%, it is defined as dense arrangement.

In this way, since a magnetic moment can be increased by setting the shim coils 21 to dense arrangement, it is possible to perform correction of a magnetic field with a current smaller than that in the first conventional example (see FIG. 12). Moreover, by employing the dense arrangement, magnetic field ripples due to the shim coils 21 which are distributed do not cause any problem.

The magnetic field adjustment device 2 according to this embodiment will be additionally described below with reference to FIG. 3. FIG. 3 is a schematic diagram illustrating the configuration of the magnetic field adjustment device 2 according to this embodiment.

The magnetic field adjustment device 2 includes the shim coil array 20 in which a plurality of shim coils 21 are arranged in the circumferential direction and the axial direction, a magnetic field measuring unit 22 that measures a magnetic field of the magnetic field evaluation surface 13 (see FIG. 1), and a current generating unit 23 that calculates a current which should flow in each shim coil 21 on the basis of a measured magnetic field value measured by the magnetic field measuring unit 22 and causes currents to flow in the shim coils 21. In addition, the current generating unit 23 includes an eigenmode strength calculating unit 24, a residual calculating unit 25, a current correction command value calculating unit 26, a summing amplifier (a power supply) 27, and a storage unit 28 as a first calculation unit 35 and includes a spherical surface harmonic function calculating unit 31 and a calculation converting unit 32 as a second calculation unit 36. The magnetic field adjustment device 2 further includes a display device 33 that displays information of the calculation results of the spherical surface harmonic function calculating unit 31 or the spherical surface harmonic function into which the eigenmode strengths are converted by the calculation converting unit 32. The magnetic field adjustment device 2 further includes an input device 34 that can designate coefficients of order terms of a target spherical surface harmonic function.

The eigenmode strength calculating unit 24 calculates an eigenmode strength on the basis of the measured magnetic field value measured by the magnetic field measuring unit 22. It is noted that the calculation process of the eigenmode strength calculating unit 24 will be described later with reference to FIGS. 4 and 5.

The residual calculating unit 25 calculates a difference (a residual) between the eigenmode strength calculated by the eigenmode strength calculating unit 24 and an eigenmode reference strength stored in the storage unit 28. The current correction command value calculating unit 26 calculates a current correction command value on the basis of the residual calculated by the residual calculating unit 25. The summing amplifier (the power supply) 27 adds the current correction command value calculated by the current correction command value calculating unit 26 to a reference current value stored in the storage unit 28 to calculate a current command value and causes a current to flow in the shim coils 21 on the basis of the calculated current command value. It is noted that the summing amplifier (the power supply) 27 is configured such that currents flowing in the shim coils 21 can be independently controlled. It is noted that the processes of the residual calculating unit 25, the current correction command value calculating unit 26, and the summing amplifier (the power supply) 27 will be described later with reference to FIGS. 4 and 6. A method of expanding a measured magnetic field to eigenmode strengths and setting a difference from a target mode strength as a residual has been described above. On the other hand, there is a calculation method of calculating a difference (a residual magnetic field) between a target magnetic field such as a uniform magnetic field and a measured magnetic field and setting mode expansion thereof as the residual from the eigenmode strength. Both methods adjust the residual magnetic field to 0.

The storage unit 28 stores data required for adjustment of a magnetic field, such as an eigenmode reference strength, a reference current value, a target magnetic field value which will be described later, and eigen distribution data.

The spherical surface harmonic function calculating unit 31 acquires order terms by expanding a spherical surface harmonic function on the basis of the measured magnetic field value measured by the magnetic field measuring unit 22.

The calculation converting unit 32 calculates correspondence between the eigenmodes and the order terms acquired by expanding the spherical surface harmonic function which will be described later.

<Magnetic Field Adjustment Method Using Magnetic Field Adjustment Device>

Figure 4:
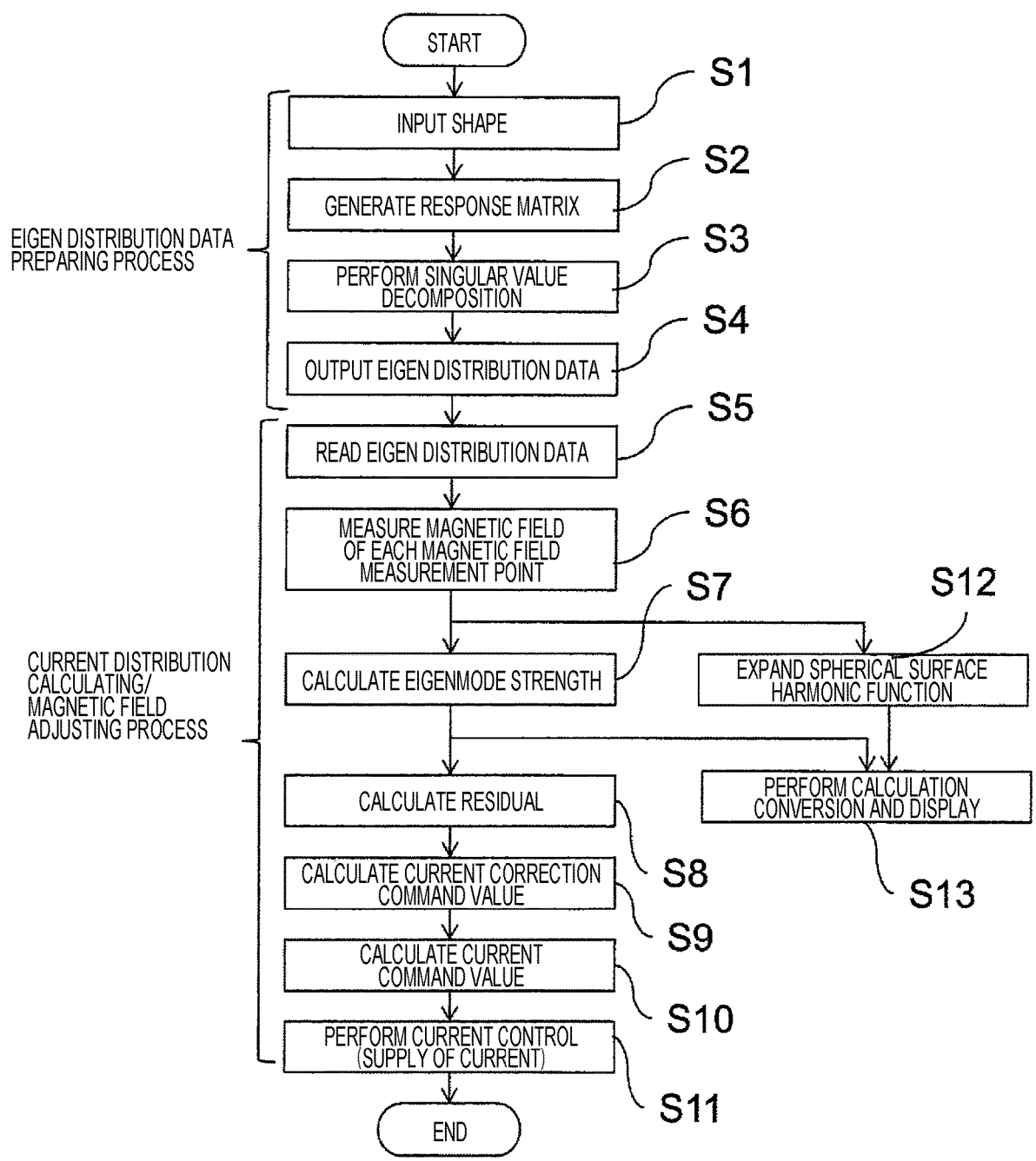
FIG. 4 is a flowchart illustrating a magnetic field adjusting method using the magnetic field adjustment device according to the embodiment.

A magnetic field adjustment method using the magnetic field adjustment device 2 according to this embodiment will be described below with reference to FIG. 4. FIG. 4 is a flowchart of a magnetic field adjustment method using the magnetic field adjustment device 2 according to this embodiment.

Steps S1 to S4 are processes of preparing eigen distribution data which is used for a current distribution calculating and magnetic field adjusting process (Steps S5 to S11) which will be described later in advance using a general-purpose computer or the like (an eigen distribution data preparing process).

In Step S1, the computer receives an input of an arrangement of the shim coils 21 constituting the shim coil array 20 (see FIG. 2) and positions of a plurality of magnetic field measurement points which are set on the magnetic field evaluation surface 13 (see FIG. 1). An operator inputs the arrangement of the shim coils 21 constituting the shim coil array 20 (see FIG. 2) and the positions of a plurality of magnetic field measurement points which are set on the magnetic field evaluation surface 13 (see FIG. 1) to the computer (a shape inputting).

In Step S2, a processor of the computer generates a response matrix A of a magnetic field on the basis of the input shape (the arrangement of the shim coils 21 and the positions of the magnetic field measurement points).

Here, the number of shim coils 21 constituting the shim coil array 20 is defined as n and an n-dimensional vector having shim coils currents of each shim coil 21 ($I_1, \ldots, I_i, \ldots, I_n$) as elements is defined as a current vector I. The number of magnetic field measurement points is defined as h and a h-dimensional vector having magnetic fields ($B_1, \ldots, B_k, \ldots, B_h$) of the magnetic field measurement points as elements is defined as a magnetic vector B. The response matrix equation of a magnetic field can be expressed as follows.

$$B = AI \quad (1)$$

The response matrix A of a magnetic field is a matrix of h rows and n columns.

Specifically, the response matrix A of a magnetic field is generated by calculating response magnetic fields of the magnetic field measurement points when a unit current flows in a certain shim coil 21 using Biot-Savart equation and performing this calculation on all the shim coils 21 in the same way.

In Step S3, the processor of the computer performs singular value decomposition on the response matrix A of a magnetic field generated in Step S2.

When the response matrix A of a magnetic field is subjected to singular value decomposition, the eigen distribution of the magnetic field distribution is expressed as follows.

$$u_1, u_2, u_3, \quad (2)$$

An eigen distribution of a current potential is expressed as follows.

$$v_1, v_2, v_3, \quad (3)$$

$u_j$ and $v_j$ satisfy the following equation.

$$\lambda_j \cdot u_j = A \cdot v_j \quad (4)$$

Here, $\lambda_j$ denotes a singular value of the j-th mode.

That is, the unit current $v_j$ of the j-th mode is an n-dimensional vector $(v_{1j}, \ldots, v_{ij}, \ldots, v_{nj})$ indicating a current distribution in which the magnetic field $u_j$ (the h-dimensional vector) of the j-th mode is generated with a strength of $\lambda_j$ (scalar), and a distribution strength corresponding to the i-th shim coil 21 is $v_{ij}$.

In Step S4, the processor of the computer outputs data of the eigenmodes (one eigenmode is represented by two eigen distributions $u_j$ and $v_j$ and one singular values $\lambda_j$) group which are acquired by singular value decomposition in Step S3 as eigen distribution data. It is noted that it is assumed that the eigenmodes are numbered sequentially from the largest singular value. The number of eigenmodes is equal to or less than the smaller of the number of shim coils 21 n and the number of magnetic field measurement points h. Accordingly, it is preferable that the number of magnetic field measurement points h be equal to or greater than the number of shim coils 21 n.

Then, in Steps S5 to S11, processes of calculating currents flowing in the shim coils 21 from the previously prepared eigen distribution data and the measured magnetic field values measured by the magnetic field measuring unit 22 and causing the currents to flow into the shim coils 21 to adjust the magnetic field are performed (the current distribution calculating and magnetic adjusting process). It is noted that when the magnetic field is adjusted, currents of reference current values $(I_{01}, \ldots, I_{0i}, \ldots, I_{0n})$ flow into the shim coils 21 as shim coil currents. It is noted that a reference current value vector $I_0$ which is an n-dimensional vector having the reference current values $(I_{01}, \ldots, I_{0i}, \ldots, I_{0n})$ of the n shim coils 21 as elements is estimated from the previous current values or a manufacturing error of the magnet device 1 (the superconductor coils 1a) that generate a main magnetic field.

In Step S5, the current generating unit 23 of the magnetic field adjustment device 2 reads the eigen distribution data prepared in advance in Step S4 and stores the read eigen distribution data in the storage unit 28. It is noted that it is assumed that a target magnetic field value distribution $B_0$ which is a h-dimensional vector having target magnetic field values $(B_{01}, \ldots, B_{0k}, \ldots, B_{0h})$ of the h magnetic field measurement points as elements is stored in advance in the storage unit 28.

In Step S6, the magnetic field measuring unit 22 of the magnetic field adjustment device 2 measures the measured magnetic field values $(B_1, \ldots, B_k, \ldots, B_h)$ of the magnetic field measurement points. The h-dimensional vector having the measured magnetic field values $(B_1, \ldots, B_k, \ldots, B_h)$ of the h magnetic field measurement points as elements is referred to as a measured magnetic field value distribution B.

In Step S7, the eigenmode strength calculating unit 24 of the magnetic field adjustment device 2 calculates the eigenmode strengths of the magnetic fields in the modes from the measured magnetic field value distribution B $(B_1, \ldots, B_k, \ldots, B_h)$. That is, the number of eigenmodes which are used for control of a magnetic field is defined as m, and the eigenmode strength $P_1$ of the magnetic field of the first mode to the eigenmode strength $P_m$ of the m-th mode are calculated. The number of eigenmodes m which are used for control of a magnetic field is equal to the number of shim coils 21 n or less than n, and it is assumed that the number of eigenmodes m is less than n. Details thereof will be described later.

Here, the eigenmode strength $P_j$ of the magnetic field in the j-th mode is calculated by the following inner product.

$$P_j = B \cdot u_j \quad (5)$$

Here, $u_j$ denotes the eigen distribution $u_j$ (with h dimensions) of the magnetic field distribution of the j-th mode and is stored as the eigen distribution data in the storage unit 28.

Furthermore, the eigenmode reference strengths of the eigenmodes are calculated from the target magnetic field value distribution $B_0$. The eigenmode reference strength $P_{0j}$ of the magnetic field in the j-th mode is calculated by the following inner product.

$$P_{0j} = B_0 \cdot u_j \quad (6)$$

It is noted that the eigenmode reference strength $P_{0j}$ may be calculated in advance and stored in the storage unit 28 and then may be read later.

In Step S8, the residual calculating unit 25 calculates a residual $\Delta P$ which is a difference between the eigenmode strength and the eigenmode reference strength for each mode. That is, the residuals which are differences between the eigenmode strengths and the eigenmode reference strengths are calculated for the first mode to the m-th mode.

Here, the residual $\Delta P_j$ of the j-th mode is calculated using the eigenmode strength $P_j$ of the j-th mode and the eigenmode reference strength $P_{0j}$ of the j-th mode as follows.

$$\Delta P_j = P_{0j} - P_j \quad (7)$$

In Step S9, the current correction command value calculating unit 26 calculates a current correction command value $\Delta I_i$ for cancelling the residual $\Delta P$. Here, the target magnetic field value distribution $B_0$ is stronger than a correction value of the magnetic field which is used for correction by the magnetic field adjustment device 2 and generally satisfies $P_j \ll B_0$. Accordingly, a current correction command value vector $\Delta I$ (an n-dimensional vector having the current correction command values $(\Delta I_1, \ldots, \Delta I_i, \ldots, \Delta I_n)$ of the n shim coils 21 as elements) which is added to the shim coils 21 necessary for adjustment of a magnetic field is calculated using the following equation.

That is, the current correction command value $\Delta I_{ij}$ which is added to the i-th shim coil 21 (where I ranges from 1 to n) to cancel the residual $\Delta P_j$ of the j-th mode is calculated as follows.

$$\Delta I_{ij} = -v_{ij}\Delta P_j/\lambda_j \quad (8)$$

Here, $v_{ij}$ denotes a distribution strength corresponding to the i-th shim coil 21 in an n-dimensional vector ($v_{1j}, \ldots, v_{ij}, \ldots, v_{nj}$) which is a unit current $v_j$ of the j-th mode and is stored as eigen distribution data in the storage unit 28. In addition, $\lambda_j$ denotes a singular value of the j-th mode and is stored as eigen distribution data in the storage unit 28. It is noted that in Equation (8), a sign "−" in the right side means that this adjustment of a magnetic field is subjected to negative feedback control of the magnetic field distribution (negative feedback control).

Accordingly, the current correction command value $\Delta I_i$ which is added to the i-th shim coil 21 to cancel the residuals ($\Delta P_1$ to $\Delta P_m$) of from the first mode to the m-th mode is expressed as follows.

$$\Delta I_i = \Delta I_{i1} + \Delta I_{i2} + \ldots + \Delta I_{im} \quad (9)$$

By performing this process on from the first shim coil 21 to the n-th shim coil 21 in the same way, the current correction command value vector $\Delta I$ ($\Delta I_1, \ldots, \Delta I_i, \ldots, \Delta_n$) is calculated.

In Step S10, the summing amplifier 27 calculates the current correction command value vector I by adding a current correction command value vector $\Delta I$ calculated by the current correction command value calculating unit 26 to the reference current value vector $I_0$. It is noted that the current command value vector I is an n-dimensional vector.

That is, regarding the i-th (where i ranges from 1 to n) shim coil 21, the current correction command value $\Delta I_i$ calculated by the current correction command value calculating unit 26 is added to the reference current value $I_{0i}$ to calculate a current command value $I_i$ which is a current flowing into the i-th (where i ranges from 1 to n) shim coil 21.

$$I_i = I_{0i} + \Delta I_i \quad (10)$$

Here, the current command value vector I can be considered to be a sum of components of the eigenmodes.

$$I = Ie_1 + Ie_2 + \ldots + Ie_j + \ldots + Ie_m \quad (11)$$

Here, $Ie_j$ denotes a current value in the j-th mode and is a sum of the j-th mode component of the reference current value vector $I_0$ and the current correction command values $\Delta Ie_j$ ($\Delta I_{1j}, \Delta I_{2j}, \ldots, \Delta I_{ij}, \ldots, \Delta I_{nj}$) which are added to the shim coils 21 to cancel the residual $\Delta P_j$ of the j-th mode.

In Step S11, the summing amplifier 27 supplies currents to the shim coils 21 on the basis of the current command value vector I. That is, a current is supplied to the i-th (where i ranges from 1 to n) shim coil 21 on the basis of the current command value $I_i$ calculated in Step S10.

In Step S12, the spherical surface harmonic function calculating unit 29 reads the measured magnetic field distribution acquired by the magnetic field measuring unit 22 from the storage unit 28 and expands the measured magnetic field distribution using a spherical surface harmonic function. A target magnetic field distribution is also read from the storage unit 28 in this way and is expanded on the basis of a spherical surface harmonic function. The order terms acquired by the expansion are stored in the storage unit 28.

In Step S13, the calculation converting unit 32 calculates correspondence between the eigenmodes based on the SVD and the order terms of the spherical surface harmonic function.

As described above, the magnetic field adjustment device 2 according to this embodiment can generate an adjusted magnetic field to decrease a residual for each eigenmode of the magnetic field. It is noted that since the eigenmodes do not interfere with each other, the residuals of the other eigenmodes do not increase even when the current of the shim coil 21 is controlled such that the residual of a certain eigenmode is decreased, and it is possible to facilitate adjustment of a magnetic field.

<Eigenmode Strength Calculating Unit 24>

Figure 5:
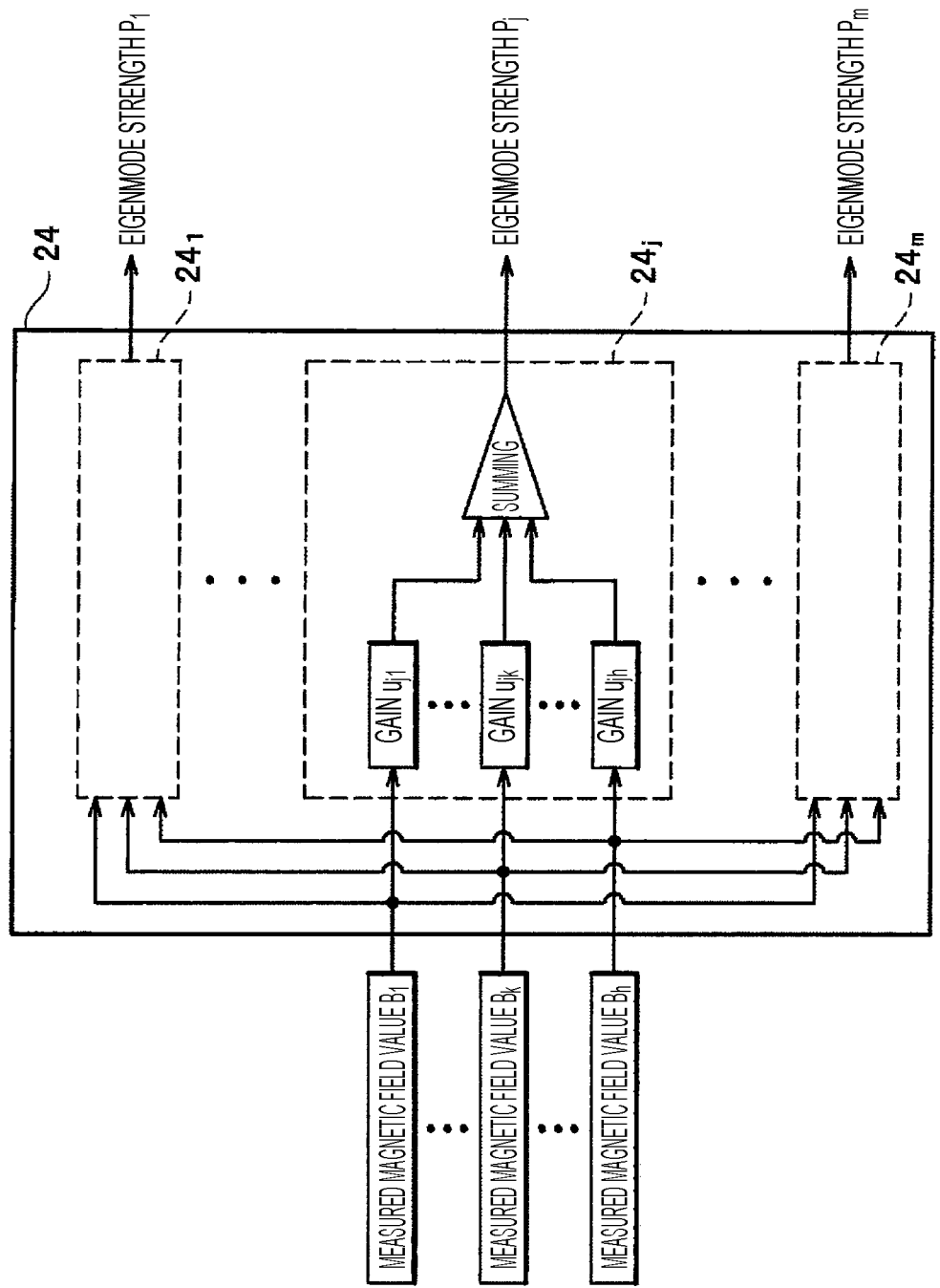
FIG. 5 is a schematic diagram of a calculation circuit of an eigenmode strength calculating unit.

Then, the calculation circuit of the eigenmode strength calculating unit 24 that calculates the eigenmode strengths $P_1$ to $P_m$ of the magnetic field in Step S7 in FIG. 4 will be additionally described below with reference to FIG. 5. FIG. 5 is a schematic diagram of the calculation circuit of the eigenmode strength calculating unit 24.

In FIG. 5, the calculation circuits denoted by reference signs $24_1$ to $24_m$ are circuits that perform the inner product of above-mentioned Equation (5) and performs calculation for all the eigenmodes (1 to m). The eigenmode strength calculating unit 24 receives an input of the measured magnetic field values ($B_1, \ldots, B_k, \ldots, B_h$) of the h magnetic field measurement points and outputs m eigenmode strengths ($P_1, \ldots, P_j, \ldots, P_m$).

It is noted that as described above, it is assumed that the number of eigenmodes m which are used for control of a magnetic field is less than the number of shim coils 21 n. As described above, the eigenmodes are numbered sequentially from the largest singular value. In an eigenmode with a small singular value (the (m+1)-th mode or subsequent eigenmodes), the value of the magnetic field generated per unit current is small as expressed by Equation (4). Accordingly, when control is performed such that the residual of a high-order eigenmode (with a small singular value) is decreased (see Steps S8 to S10), a large current is required. It is noted that as described above in Step S4, since the maximum number of eigenmodes is determined to be the smaller value of the number of shim coils 21 n and the number of magnetic field measurement points h and the number of magnetic field measurement points h is set to be equal to or greater than the number of shim coils 21 n, the maximum number of eigenmodes is determined to be the number of shim coils 21 n. Accordingly, the number of eigenmodes m which are used for control of a magnetic field is set to a small value (smaller than the number of shim coils 21 n) to adjust the magnetic field with a small current. It is noted that when the number of eigenmodes m which are used for control of a magnetic field is excessively small, the required magnetic field accuracy may not be achieved and thus m is appropriately set depending on the required magnetic field accuracy.

The calculation circuits $24_1$ to $24_m$ have the same configuration and thus an example of the calculation circuit $24_j$ will be described below. The calculation circuit $24_j$ includes h amplifier circuits that amplify an input signal (amplify a gain) and a summing circuit, performs calculation expressed by Equation (5A), and outputs the eigenmode strength $P_j$ of the j-th mode. It is noted that the magnetic field distribution $u_j$ ($u_{j1}, \ldots, u_{jk}, \ldots, u_{jh}$) of the j-th mode is stored as eigen distribution data in the storage unit 28.

$$P_j = B_1 u_{j1} + \ldots + B_k u_{jk} + B_h u_{jh} \quad (5A)$$

The calculation circuit of the eigenmode strength calculating unit 24 in FIG. 5 can implement the inner product expressed by above-mentioned Equation (6) that outputs the eigenmode reference strength $P_{0j}$ with the target magnetic field value distribution $B_0$ as an input.

<Residual Calculating Unit 25, Current Correction Command Value Calculating Unit 26, and Summing Amplifier 27>

Figure 6:
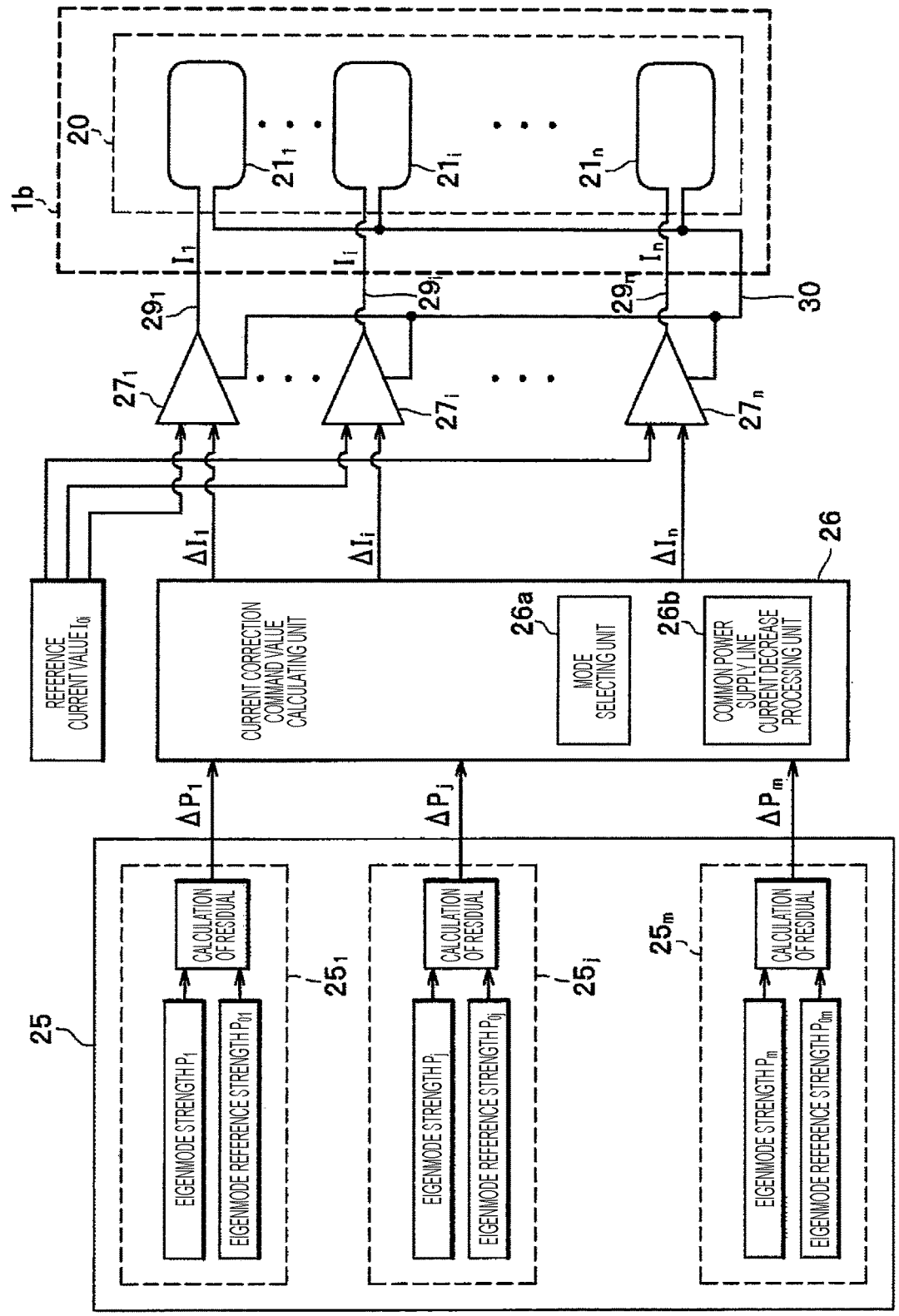
FIG. 6 is a schematic diagram illustrating calculation circuits of a residual calculating unit, a current correction command value calculating unit, and a summing amplifier and connection to shim coils.

Then, the calculation circuits of the residual calculating unit 25, the current correction command value calculating unit 26, and the summing amplifier 27 will be additionally described below with reference to FIG. 6. FIG. 6 is a schematic diagram illustrating the calculation circuits of the residual calculating unit 25, the current correction command value calculating unit 26, and the summing amplifier 27 and connection to the shim coils 21.

The residual calculating unit 25 includes residual calculation circuits $25_1$ to $25_m$, receives an input of m eigenmode strengths ($P_1, \ldots, P_j, \ldots, P_m$) and m eigenmode reference strengths ($P_{O1}, \ldots, P_{Oj}, \ldots, P_{Om}$) output from the eigenmode strength calculating unit 24 (see FIG. 5), performs the residual calculation of Equation (7), and outputs m residuals ($\Delta P_1, \ldots, \Delta P_j, \ldots, \Delta P_m$) (see Step S8 in FIG. 4).

The current correction command value calculating unit 26 receives an input of m residuals ($\Delta P_1, \ldots, \Delta P_j, \ldots, \Delta P_m$), performs the calculations expressed by Equations (8) and (9), and outputs n current correction command values ($\Delta I_1, \ldots, \Delta I_i, \ldots, \Delta I_n$) (see Step S9 in FIG. 4).

The summing amplifier 27 receives an input of n reference current values ($\Delta I_{O1}, \ldots, \Delta I_{Oi}, \ldots, \Delta I_{On}$) and n current correction command values ($\Delta I_1, \ldots, \Delta I_i, \ldots, \Delta I_n$), performs the calculation of Equation (10), and calculates n current command values ($I_1, \ldots, I_i, \ldots, I_n$) (see Step S10 in FIG. 4). Then, the summing amplifier 27 performs control such that the currents flowing in the shim coils $21_1$ to $21_n$ reach the current command values ($I_1, \ldots, I_i, \ldots, I_n$).

Here, the summing amplifier 27 includes independent summing amplifiers $27_1$ to $27_n$ the summing amplifiers $27_1$ to $27_n$ are connected to ends on one side of the shim coils $21_1$ to $21_n$ via the first power supply lines $29_1$ to $29_n$ in a one-to-one correspondence manner and are configured to independently control the currents of the shim coils $21_1$ to $21_n$.

In addition, the ends on the other side of the shim coils $21_1$ to $21_n$ are connected to the summing amplifiers $27_1$ to $27_n$ via the second power supply line 30 which is a common power supply line. Here, the power supply lines 29 and 30 that connect the shim coils 21 in the refrigerant container 1b (and the vacuum container 1d) which is an extremely low-temperature portion and the summing amplifier 27 outside the refrigerant container 1b serve as an entrance of heat to the extremely low-temperature portion. In the first conventional example, two current introduction terminals are used for a single shim coil. That is, when the number of shim coils is defined as n, 2n wires serve as heat entrance ports that penetrate a vacuum heat insulation portion. On the other hand, in this embodiment, one of the power supply lines to each shim coil 21 is set to a common power supply line (the second power supply line 30) as illustrated in FIG. 5. Accordingly, (n+1) wires serve as heat invasion ports that penetrate the vacuum heat insulation portion and can decrease the number of wires and curb invasion of heat to the extremely low-temperature portion. It is noted that the second power supply line 30 may be earth wire.

When the currents flowing in the shim coils $21_1$ to $21_n$ are changed at the time of current control, magnetic interference between the shim coils 21 occurs and thus the currents should be controlled with high accuracy. On the other hand, when the currents flowing in the shim coils $21_1$ to $21_n$ reach a predetermined value (the current command value), interference does not occur and current control is not necessary. Accordingly, a permanent current switch (PCS) (not illustrated) may be provided between terminals of each of the shim coils $21_1$ to $21_n$ and the shim coils may operate in a permanent current mode. That is, after the currents flowing in the shim coils 21 are controlled to the current command values by the summing amplifier 27, the permanent current switches (not illustrated) are connected. By employing this configuration, the shim coils 21 for adjustment of a magnetic field in addition to the superconductor coils 1a (see FIG. 1) can operate in the permanent current mode.

It is noted that in a SVD type shim coils which correspond to the eigenmode strengths in a one-to-one correspondence manner, the summing circuit illustrated in FIG. 6 is not provided and the other configuration is the same. The second power supply line 30 can also be installed. Since high-order eigenmodes are not present in the SVD type shim coils, at least one dummy coil is provided. Regarding the dummy coil, a circuit including the dummy coil is supplied with a current such that a magnetic field generated due to the current flowing through the second power supply line 30 is substantially zero in combination of a circuit (a high-order shim coil) generating a very weak magnetic field with the shim coils. There is also a method of forming a negative shim coil that generates a magnetic field opposite to that of the used shim coils, adjusting the magnetic field thereof using the magnetic field differences (high-order components) thereof, and adjusting the current using the sum thereof such that the current in the second power supply line 30 is substantially zero. In this case, a thick power supply line is not necessary and thus it is possible to curb invading heat.

As illustrated in FIG. 6, the current correction command value calculating unit 26 may also include a mode selecting unit 26a. The mode selecting unit 26a sets the coefficient to $G_j=0$ on the basis of a preset allowable error E when the residual $\Delta P_j$ of the j-th mode satisfies the following conditions.

$$\Delta P_j < \varepsilon \qquad (12)$$

When Equation (12) is not satisfied, the coefficient is set to $G_j=1$.

The current correction command value calculating unit 26 performs calculation by replacing above-mentioned Equation (9) with the following Equation (9A) including the coefficient $G_j$.

$$\Delta I_i = \Sigma_j - G_j v_{ij} \Delta P_j / \lambda_j \qquad [\text{Math. 1}]$$

That is, when the residual $\Delta P_j$ of the j-th mode is less than the allowable error $\varepsilon$, the j-th mode may be excluded from the summing, that is, adjustment of a magnetic field in the j-th mode may not be performed. When the residual $\Delta P_j$ is sufficiently small (less than the allowable error $\varepsilon$), $\Delta I_{ij}$ also decreases as expressed by Equation (8). Accordingly, when the adjustment of a magnetic field is performed in the same way, there is a concern that uniformity of a magnetic field will be disturbed depending on a current controllable resolution of the summing amplifier (the power supply) 27. On the other hand, when the residual $\Delta P_j$ of the j-th mode is less than the allowable error $\varepsilon$, it is possible to prevent such disturbance in uniformity of the magnetic field by not performing the adjustment of a magnetic field for the j-th mode. It is noted that 0 or 1 is used as $G_j$, but the invention is not limited thereto and another value may be used.

As illustrated in FIG. 6, the current correction command value calculating unit 26 may include a common power supply line current decrease processing unit 26b.

Here, currents $I_1$ to $I_n$ flows in the first power supply lines $29_1$ to $29_n$ causing currents to flow in the first to n-th shim coils $21_1$ to $21_n$ respectively, but the current $I_{com}$ flowing in the second power supply line 30 which is the common power supply line is as follows.

$$I_{com}=I_1+\ldots+I_i+\ldots+I_n \quad (13)$$

Accordingly, since a larger current than that in the first power supply lines $29_1$ to $29_n$ flows in the second power supply line 30, a current capacity is set to be large, that is, a sectional area of a wire of the second power supply line 30 is set to be large. Accordingly, there is concern that the invasion of heat from the second power supply line 30 will increase.

In this regard, the common power supply line current decrease processing unit 26b controls the current $I_{com}$ flowing in the second power supply line 30 such that it decreases. As described above, the first to m-th eigenmodes are used for control of a magnetic field, and the number thereof is less than the number of shim coils 21 $n$ (m<n). Accordingly, a degree of freedom (n−m) is left. As described above, as the eigenmode has a higher order (degree), the singular value thereof becomes smaller and the magnetic field value generated per unit current becomes smaller. Accordingly, even when the currents flowing into the shim coils 21 are changed in a high-order eigenmode, an influence to the magnetic field is small. On the other hand, the current $I_{com}$ flowing into the second power supply line 30 can be decreased. Accordingly, it is not necessary extremely increase the sectional area of the wire of the second power supply line 30 and the capacity thereof can be decreased to not more than about three times compared to that of the first power supply lines $29_1$ to $29_n$, for example, to about 1/10 thereof by more active control. Accordingly, it is possible to decrease the sectional area of the wire of the second power supply line 30 and to curb invasion of heat from the second power supply line 30.

Here, the current distribution vector $I_H$ in a high-order mode is defined as follows.

$$I_H=F_{m+1}v_{m+1}+\ldots+F_nv_n \quad (14)$$

It is noted that $v_{m+1}$ (to $v_n$) is a unit current (an n-dimensional vector) of the (m+1 (to n))-th mode and is stored as eigen distribution data in the storage unit 28. $F_{m+1}$ to $F_n$ are coefficients.

The summing amplifier 27 controls the currents flowing into the shim coils 21 using the current command value vector I, but an influence to a magnetic field is small even when the current distribution vector $I_H$ in a high-order mode is added thereto. Accordingly, the common power supply line current decrease processing unit 26b determines $F_{m+1}$ to $F_n$ such that the current flowing into the second power supply line 30 decreases.

For example, the n-th mode having a smallest influence to a magnetic field, that is, having a smallest singular value, can be used to calculate the followings.

$$F_{m+1}=\ldots=F_{n-1}=0$$

$$F_n=-I_{com}/(v_{1n}+\ldots+v_{in}+\ldots+v_{nn}) \quad (15)$$

Here, $v_{in}$ denotes a current distribution strength corresponding to the i-th shim coil 21 of the unit current $v_n$ (an n-dimensional vector) of the n-th mode.

It may also be difficult to calculate a high-order mode. This is because a calculation error increases relatively as the singular value decreases. In this case, a current distribution of a virtual mode is considered for the current distribution vector $I_H$ in a high-order mode. First, the following n-dimensional vector is considered.

$$E=(1,1,\ldots,1) \quad (16)$$

$v_H$ is calculated as follows.

$$v_H=E-(Ev_1+\ldots+Ev_L)/|E-((Ev_1+\ldots+Ev_L))| \quad (17)$$

Here, L is a component of E and the L-th or lower eigenmode is not included in the $v_H$ by subtracting the L-th eigenmode. In addition, L is an integer which is equal to or greater than m+1 and less than n. The current distribution vector $I_H$ in a high-order mode calculated by the following equations using the current distribution $v_H$ calculated in this way is supplied to the shim coil currents.

$$I_H=F_HV_H \quad (14A)$$

$$F_H=-I_{com}/(v_{1H}+\ldots+v_{iH}+\ldots+v_{nH}) \quad (15A)$$

The current passing through the second power supply line (the common power supply line) 30 can be kept small in this way.

The current distribution vector $I_H$ in a high-order mode may be output from the current correction command value calculating unit 26 to the summing amplifier (the power supply) 27, and the current distribution vector $I_H$ in a high-order mode may be added when the current correction command value vector ΔI is added to the reference current value vector $I_0$ with the summing amplifier (the power supply) 27. Furthermore, the result obtained by adding the current distribution vector $I_H$ in a high-order mode to the current correction command value vector ΔI in the current correction command value calculating unit 26 may be output as the current correction command value vector ΔI to the summing amplifier (the power supply) 27.

<<Spherical Surface Harmonic Function Calculating Unit 31>>

The spherical surface harmonic function calculating unit 31 expands the measured magnetic field distribution acquired by the magnetic field measuring unit 22 using a spherical surface harmonic function. A target magnetic field distribution is also expanded on the basis of the spherical surface harmonic function. It is noted that the spherical surface harmonic function calculating unit 31 may receive an input of information on target uniformity of a magnetic field distribution or a target strength of the spherical surface harmonic function (coefficients of the order terms) via the input device 34 from the outside.

Calculation which is performed by the spherical surface harmonic function calculating unit 31 can be expressed by Equation (15).

$$B_z(r,\theta,\phi)=\Sigma r^n \Sigma P_n^m(\cos\theta)\{\text{Anm}\cos(m\phi)+\text{Bnmm}\sin(m\phi)\} \quad (15)$$

Here, Equation (15) is calculated in the range of m of 0 to n and the range of n of 0 to ∞. $P_n^m$ denotes an associated Legendre function. Here, r denotes a position with respect to the center, θ denotes an angle by circulation in the magnetic field direction, and φ denotes an angle with respect to the magnetic field direction. By expanding the magnetic field in this way, an MRI operator often understands a magnetic field state with attention to the coefficients Anm and Bnm. Therefore, the magnetic field adjustment device 2 according to this embodiment enables an operator to understand details of the magnetic field adjustment based on the above-mentioned singular value decomposition using the coefficients of the spherical surface harmonic function. Accordingly, an operator can understand the magnetic field state on the basis of the same parameters as in the conventional case, and it is possible to adjust the magnetic field with high accuracy using the singular value decomposition. The conversion between the eigenmodes acquired by the singular value decomposition and the coefficients of the order terms acquired by expanding the spherical surface harmonic function is performed as follows by the calculation converting unit 32.

<<Calculation Converting Unit 32>>

The calculation converting unit 32 performs conversion between the eigenmodes and the coefficients of the spherical surface harmonic function. For example, in above-mentioned Equation (15), the magnetic field distribution in the case of n=i and m=j is calculated at each magnetic field measurement point. As a result, a vector $B_zij$ of the magnetic field strength is acquired and conversion from Anm and Bnm to the eigen distributions based on the singular value decomposition is performed by calculating the inner product of the vector $B_zij$ and a vector Bk of the magnetic field distribution acquired from the eigenmodes as expressed by Equation (5). On the other hand, conversion from the eigenmode magnetic field distribution $u_k$ to Anm and Bnm can be performed by integrating the inner product of the eigen distribution $u_k$ and $B_z$ (r, θ, φ) with respect to θ and φ on the magnetic field measurement (evaluation) surface. As a result, both can be expressed by the following matrix equation.

$$P=C(Anm, Bnm) \quad (16)$$

P is a vector having the eigenmode strengths $P_j$ as elements, and (Anm, Bnm) is a vector having Aij and Bij as elements. In general, the order terms in which i and j are equal to or less than about 15 are acquired by expansion of a spherical surface harmonic function, and about 225 or less SVD eigenmodes are acquired. Accordingly, C can be a square matrix of about 15×15. In this case, the coefficients of the order terms in the spherical surface harmonic function can be converted into the SVD eigenmode strengths by Equation (16), and the SVD eigenmode strengths can also be converted into the strengths of the spherical surface harmonic function (the coefficients of the order terms) by calculating an inverse matrix thereof.

By using this calculation, the strength of the spherical surface harmonic function can be displayed on the display device 33 to present an operator the magnetic field state or a control system that receives an input of the strength of the spherical surface harmonic function via the input device 34 and performs adjustment of a magnetic field can adjust a magnetic field with high accuracy using the SVD eigenmode strengths. On the other hand, a current measured magnetic field or an output of the shim coils with supply of a current thereto can be converted from the eigenmode strengths to the coefficients of the spherical surface harmonic functions and an operator's operation can also be facilitated.

EXAMPLE

An example of adjustment of a magnetic field using the magnetic field adjustment device 2 according to this embodiment will be described below with reference to FIGS. 7 to 9.

FIG. 7(a) is a developed view illustrating an arrangement of the shim coil array 20 according to an example. It is noted that the horizontal axis represents a position in the circumferential direction by radians of −π/2 to 3π/2 and the vertical axis represents a position in the axial direction by meters (m). Each shim coil 21 has a rectangular shape along a cylinder and the shim coils 21 are arranged at the same intervals of angle in the circumferential direction. Moreover, the shim coils 21 are arranged as densely as possible to generate a strong magnetic field. It is noted that the shim coils 21 do not need to be arranged by decomposing at the same angles in the circumferential direction. In FIG. 7(a), some shim coils are marked for the purpose of easy understanding of shapes. The shim coils 21 are numbered from 1 to 30.

FIG. 7(b) is a bird's-eye view illustrating the arrangement of the shim coil array 20 according to the example. A small cylindrical surface at the center is a magnetic field evaluation surface 13 on which a magnetic field is measured. In addition, the magnetic field measurement points can be set to arbitrary positions in this method. The magnetic field evaluation surface 13 is a cylindrical surface unlike FIG. 1. 30 shim coils 21 are arranged cylindrically. Each shim coil 21 includes current terminals and is not illustrated in the drawing. In each shim coil 21, a wire is generally wound not by one turn but by multiple turns. Accordingly, it is possible to decrease the current and to decrease the size of the current introduction terminals. Furthermore, this example is advantageous in view of an amount of heat emitted and is advantageous particularly when a superconductor wire is used.

The intervals between the shim coils 21 are very small but slightly gaps are actually present therebetween. This is for insulation or because the shim coils 21 are fixed components. In an actual device, a ratio of a radius of a position at which a magnetic field is controlled and a radius of a cylindrical surface on which the coils are arrangement is a ratio of about a half (about ½). Accordingly, slight gaps can be present between the shim coils 21. When the magnitude of the gaps is about ½ and about ⅕ (=about ⅒), a variation of the magnetic field due to the gaps does not cause an actual problem. That is, the conditions for the size of the shim coils 21 are considered to be that the magnitude of the gaps is about ⅒ or less and about 80% or more of the area is covered by the shim coils 21.

Figure 8:
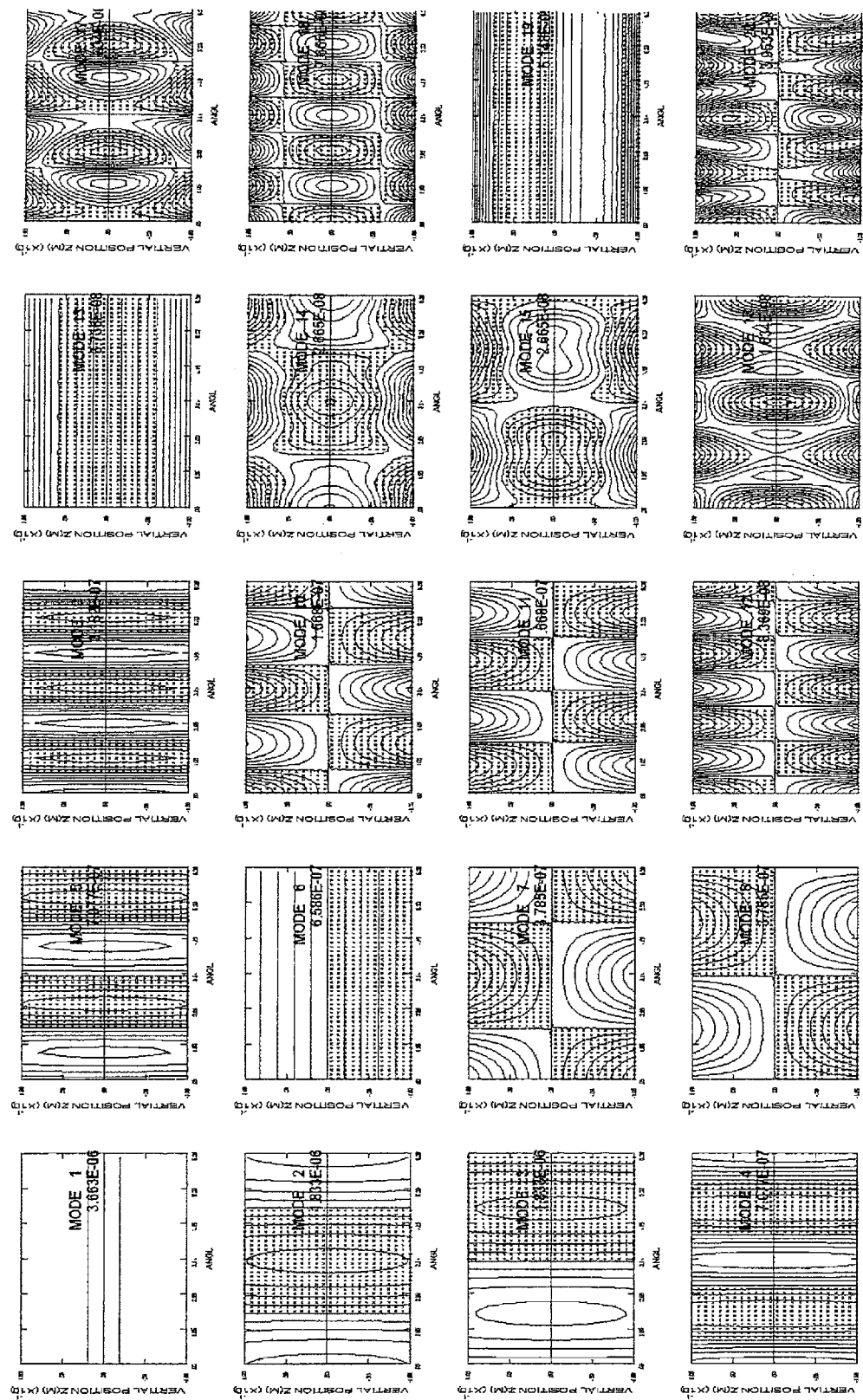
FIG. 8 is a graph illustrating a magnetic field distribution of eigenmodes according to an example.

FIG. 8 is a graph illustrating magnetic field distributions of the eigenmodes according to the example. In the shim coil array 20 (the shim coils 21) illustrated in the example of FIG. 7, the magnetic field distributions $u_j$ of the eigenmodes which can be generated on the magnetic field evaluation surface 13 are illustrated in FIG. 8. In the drawings, the horizontal axis represents a position in the circumferential direction and the vertical axis represents a position in the axial direction. A dot represents whether a sign of a magnetic field is plus or minus. Furthermore, MODE in the drawings indicates an eigenmode number and a numerical value therebelow indicates a singular value of the eigenmode. Moreover, the same number of eigenmodes as the number of coils (n=30) are possible but 20 eigenmodes (m=20) and magnetic field distributions thereof are illustrated in FIG. 8.

In FIG. 8, magnetic field components in the axial direction are illustrated as distributions for each eigenmode. However, although not illustrated explicitly, it is obvious that the magnetic field components in the radial direction can be adjusted in the same way when it is considered that the shim coils 21 are arranged in a direction in which a radial magnetic field is generated.

As illustrated in FIG. 7, the shim coils 21 in the shim coil array 20 according to the example are arranged by one layer on the cylindrical surface, but it can be understood that a plurality of eigenmodes not interfering with each other can be generated as illustrated in FIG. 8 similarly to the second conventional example. It is noted that the number of eigenmodes is equal to or less than the smaller value of the number of shim coils 21 n and the number of magnetic field measurement points h. Accordingly, a plurality of eigenmodes can be generated by arranging a plurality of shim coils 21 in both the circumferential direction and the axial direction.

Figure 9:
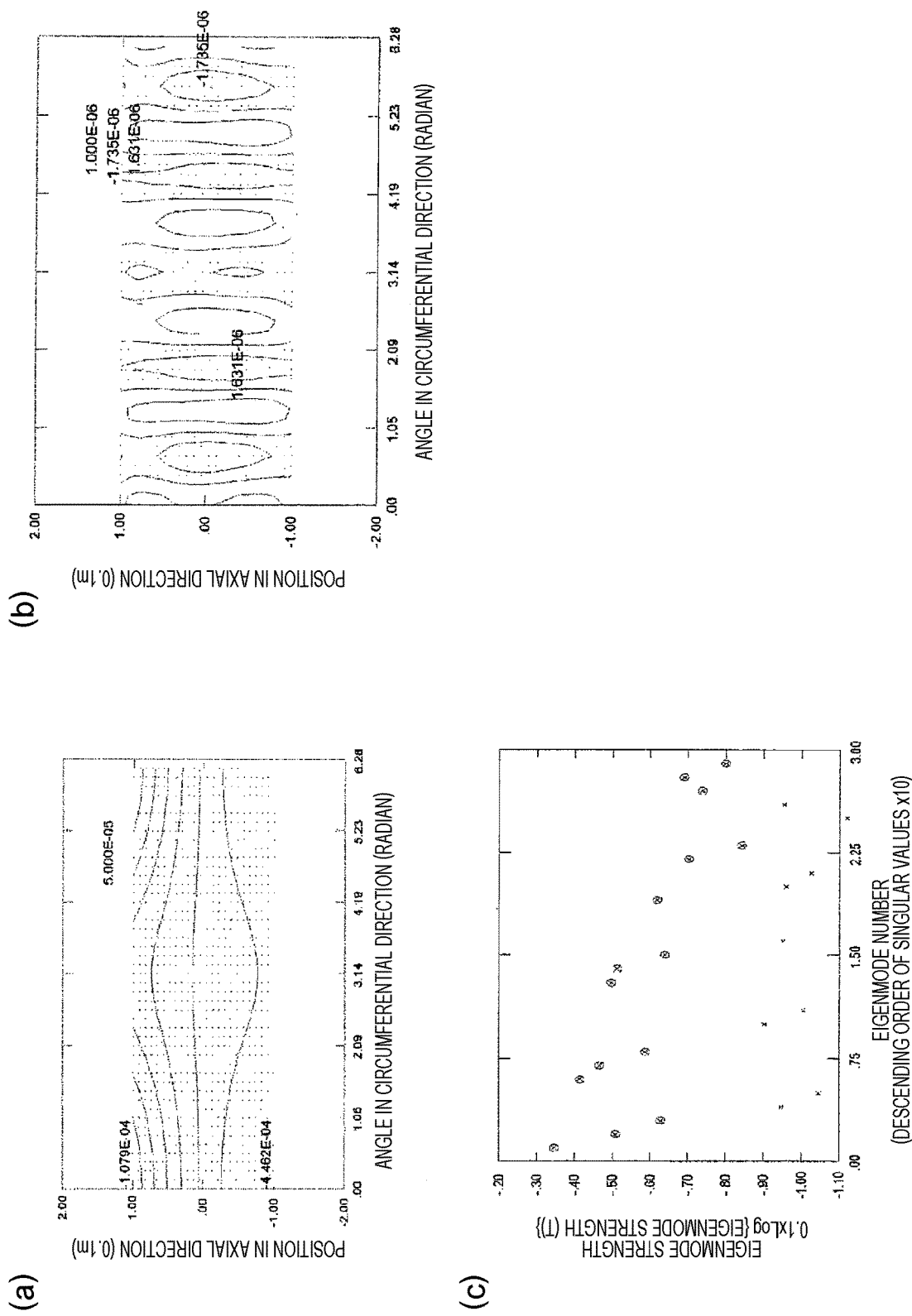
FIG. 9 is a graph illustrating a simulation example in which an error magnetic field is adjusted.

FIG. 9 is a graph illustrating an example in which adjustment of an error magnetic field is simulated.

In FIG. 9(a), an error magnetic field when one superconductor coil 1a (see FIG. 1) that generates a main magnetic field is tilted is marked by a contour line for every 0.5 Gauss ($5.000 \times 10^{-5}$ [T]). The magnetic field evaluation surface 13 is the cylindrical surface illustrated in FIG. 7(b) and has a size of ±10 cm in the vertical direction and 33.3 cm in the radial direction. As illustrated in FIG. 9(a), the error magnetic field is distributed from −1.08 Gauss ($-1.079 \times 10^{-4}$ [T]) to −4.45 Gauss ($-4.462 \times 10^{-4}$ [T]).

The eigenmode strengths are calculated from the magnetic field distribution and are numbered in the descending order of singular values, and the strengths are plotted by mark x in FIG. 9(c). The vertical axis represents the eigenmode strength of the residuals and the horizontal axis represents an eigenmode number.

As illustrated in FIG. 9(c), the graph illustrated in FIG. 9(c) has a tendency to decrease to the right side and large components of the eigenmode strengths disappear as the eigenmode number increases. This means that adjustment of a magnetic field can be suitably performed by performing control of a magnetic field on the first to m-th eigenmodes and not performing control of a magnetic field on high-order modes ((m+1)-th to n-th modes) in FIGS. 5 and 6.

When the eigenmode components marked by a circle in FIG. 9(c) are corrected, large components disappear. A residual magnetic field of about one over several hundred can be expected in view of the strengths of the components to be corrected. In this case, eigenmodes having large contribution are selected from FIG. 9(c) and considered for correction of the magnetic field. This process corresponds to the process in the mode selecting unit 26a in FIG. 6. When it is intended to correct all the eigenmodes (first to m-th eigenmodes), the current in each shim coil 21 is likely to be excessively large and thus selection of eigenmodes having large contribution to adjustment of a magnetic field is greatly significant. The graph illustrated in FIG. 9(c) is used for the selection.

FIG. 9(b) illustrates a residual magnetic field distribution when the eigenmode components marked by a circle are corrected. Here, the residual magnetic field is marked by a contour line for every 0.01 Gauss ($1.000 \times 10^{-6}$ [T]). As illustrated in FIG. 9(b), the residual magnetic field is distributed from 0.016 Gauss ($+1.631 \times 10^{-6}$ [T]) to −0.017 Gauss ($-1.735 \times 10^{-6}$ [T]). That is, the residual magnetic field has a magnitude equal to or less than ±2 µT, from which it can be seen that the magnetic field has been corrected satisfactorily.

Modified Example

The magnet device 1 and the magnetic field adjustment device 2 according to the embodiment are not limited to the configurations of the embodiment, but can be modified in various forms without departing from the gist of the invention.

FIG. 10(a) is a developed view of a shim coil array 20 according to a first modified example and FIGS. 10(b) and 10(c) illustrate examples of a magnetic field distribution of the eigenmodes of the shim coil array 20 according to the first modified example.

In FIG. 2, the widths of the shim coils 21 arranged in the axial direction are set to the same width, but the invention is not limited thereto. As illustrated in FIG. 10(a), shim coils 21B close to the center in the axial direction, that is, close to the magnetic field evaluation surface 13 (the magnetic field use area 12), may be set to have a small width and shim coils 21A far therefrom may be set to have a large width. Even when the widths are not equal to each other in this way, it is possible to obtain a magnetic field distribution of eigenmodes not interfering with each other and to adjust the magnetic field by the same process as illustrated as an example in FIGS. 10(b) and 10(c).

Figure 11:
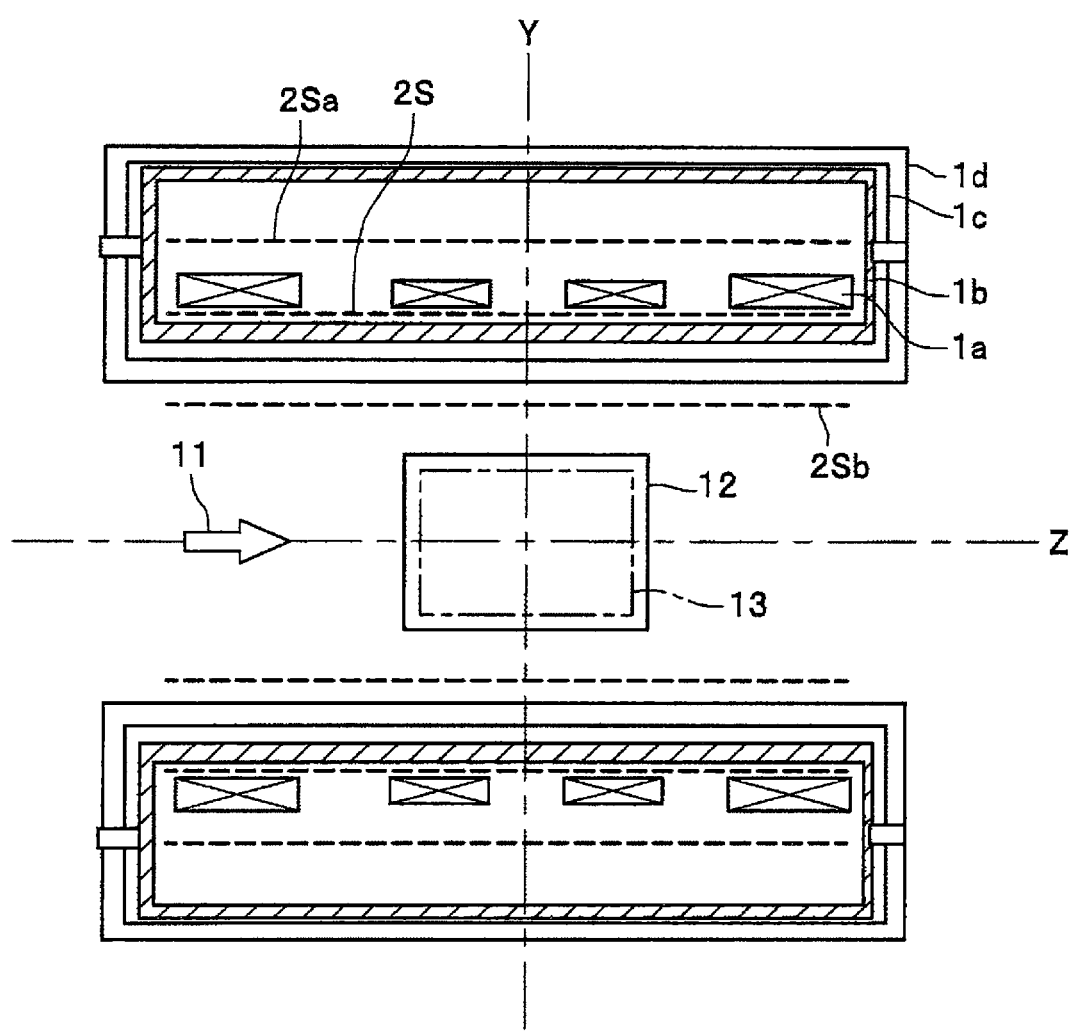
FIG. 11 is a schematic sectional view illustrating a configuration of a magnet device according to a second modified example.

FIG. 11 is a schematic sectional view illustrating a configuration of a magnet device according to a second modified example.

In FIG. 1, the shim coil array 20 is disposed on the cylindrical surface 2S, but the invention is not limited thereto.

For example, the shim coil array 20 may be disposed on a cylindrical surface 2Sa. By disposing the shim coil array 20 outside of the superconductor coils 1a, the superconductor coils 1a can be located closer to the magnetic field use area 12 (the magnetic field evaluation surface 13) in comparison with a case in which the shim coil array 20 is disposed inside of the superconductor coils 1a (see FIG. 1), and thus the currents flowing in the superconductor coils 1a can be decreased. On the other hand, since the shim coils 21 are separated farther from the magnetic field use area 12 (the magnetic field evaluation surface 13), the currents flowing in the shim coils 21 increase. From this point of view, it is preferable that the shim coil array 20 be disposed on the cylindrical surface 2S.

The shim coil array 20 may be disposed on a shim coil current surface 2Sb. In this case, the shim coil array 20 is a shim coil array which is normally conductive. Since this position is close to the magnetic field use area 12, it is possible to achieve rapider response and it is possible to correct a larger magnetic field.

In this way, the position of the shim coil array 20 can be appropriately selected in consideration of a thickness required for the arrangement, a margin of the arrangement area of the superconductor coils 1a, and magnetic field capability of the shim coils 21 required for correction of a target.

Furthermore, the magnet device 1 and the magnetic field adjustment device 2 according to the embodiment can be used for a device using a magnetic field such as an accelerator or a magnetic resonance imaging device. Moreover, the magnet device 1 according to the embodiment is a magnet device that generates a static magnetic field in a cylindrical area of the magnetic field use area 12, and the magnetic field adjustment device 2 according to the embodiment is a device that adjusts a magnetic field such that static magnetic field accuracy of the magnetic field use area 12 is improved, but the magnetic field which is generated in the magnetic field use area 12 by the magnet device 1 is not limited to the static magnetic field. The magnet device 1 and the magnetic field adjustment device 2 may generate a target magnetic field distribution in the magnetic field use area 12. In addition, the central axis (the Z axis) of the superconductor coils 1a of the magnet device 1 is horizontal, but the invention is not limited thereto and may be, for example, vertical.

The magnet device 1 according to the embodiment has a tunnel shape as illustrated in FIG. 1, but may have a general magnet shape. In FIG. 1, the magnetic field use area 12 has a cylindrical shape, but the invention is not limited thereto. For example, the magnetic field use area 12 may have a spherical shape or another shape. The magnetic field evaluation surface 13 can be appropriately selected depending on the shape of the magnetic field use area 12.

REFERENCE SIGNS LIST 1 magnet device
11 magnetic field direction
12 magnetic field use area
13 magnetic field evaluation surface
2 magnetic field adjustment device
20 shim coil array
21 shim coil
22 magnetic field measuring unit
23 current generating unit
24 eigenmode strength calculating unit
25 residual calculating unit
26 current correction command value calculating unit
26a mode selecting unit
26b common power supply line current decrease processing unit
27 summing amplifier (summing unit, power supply)
28 storage unit
29 first power supply line
30 second power supply line (common power supply line)
31 spherical surface harmonic function calculating unit
32 calculation converting unit
33 display device
34 input device
35 first calculation unit
36 second calculation unit

The invention claimed is:

1. A magnetic field adjustment device, at least comprising:
a shim coil array that includes a plurality of shim coils for adjusting a static magnetic field in a magnetic field use area;
a first calculation unit that determines current command values of the shim coils on the basis of eigenmodes which are obtained by singular value decomposition of a response matrix of currents flowing in the shim coils to a magnetic field;
a power supply that controls the currents in the shim coils on the basis of the determined current command values;
a second calculation unit that calculates correspondence between order terms which are obtained by expanding the static magnetic field in the magnetic field use area using a spherical surface harmonic function and strengths of the eigenmodes; and
a display device that is connected to the second calculation unit and displays a change of the static magnetic field in the magnetic field use area due to the shim coils supplied with the currents on the basis of the current command values as information on the order terms of the spherical surface harmonic function.

2. The magnetic field adjustment device according to claim 1,
wherein one of power supply lines from the power supply to the shim coils is configured as a common power supply line which is common to the shim coils.

3. The magnetic field adjustment device according to claim 1,
wherein the shim coil array is disposed to surround the magnetic field use area of a magnet device and to surround a center axis of the magnet device in a circumferential direction,
wherein two or more of the shim coils are arranged in the circumferential direction and two or more of the shim coils are arranged in an axial direction, and
wherein the shim coils are arranged such that a sum of areas surrounded by the shim coils occupies 80% or more of an area of a coil surface of the shim coil array.

4. The magnetic field adjustment device according to claim 1,
wherein the shim coils are disposed in a superconductive magnet device.

5. The magnetic field adjustment device according to claim 4,
wherein each of the shim coils consists of a superconductive wire and is accommodated in a refrigerant container that contains a superconductor coil of the superconductive magnet device, and
wherein a permanent current switch is provided in each of the shim coils.

6. The magnetic field adjustment device according to claim 1, comprising
a coil that is wound in the circumferential direction of the center axis and is supplied with a current on the basis of a high-order mode of the eigenmodes.

7. The magnetic field adjustment device according to claim 1,
wherein the first calculation unit includes:
an eigenmode strength calculating unit that calculates an eigenmode strength which is a strength of each eigenmode by an inner product with eigenmodes of singular value decomposition from measured magnetic field data of multiple points;
a residual calculating unit that calculates residuals which are differences between the eigenmode strengths of the eigenmodes which are calculated by the eigenmode strength calculating unit and an eigenmode reference strength of the eigenmodes corresponding to a target magnetic field distribution;
a current correction command value calculating unit that calculates a correction value of the current supplied to the shim coils in the eigenmodes by adding a coefficient which is determined on the basis of current distributions and singular values of the eigenmodes to the residuals of the eigenmodes and calculates correction command values of the currents supplied to the shim coils by summing correction values of the currents supplied to the shim coils in the eigenmodes for each shim coil; and
a summing unit that sums the correction command values calculated by the current correction command value calculating unit and a reference current value and determines the current command values for the shim coils, and
wherein negative feedback control is performed on a residual magnetic field.

8. A magnetic resonance imaging device comprising the magnetic field adjustment device according to claim 1.

* * * * *